US011116435B2

United States Patent
Urman et al.

(10) Patent No.: US 11,116,435 B2
(45) Date of Patent: Sep. 14, 2021

(54) AUTOMATIC IDENTIFICATION OF A LOCATION OF FOCAL SOURCE IN ATRIAL FIBRILLATION (AF)

(71) Applicant: BIOSENSE WEBSTER (ISRAEL) LTD., Yokneam (IL)

(72) Inventors: Roy Urman, Irvine, CA (US); Yariv Avraham Amos, Tzorit (IL)

(73) Assignee: Biosense Webster (Israel) Ltd., Yokneam (IL)

(*) Notice: Subject to any disclaimer, the term of this patent is extended or adjusted under 35 U.S.C. 154(b) by 109 days.

(21) Appl. No.: 16/550,694

(22) Filed: Aug. 26, 2019

(65) Prior Publication Data
US 2021/0059550 A1 Mar. 4, 2021

(51) Int. Cl.
*A61B 5/287* (2021.01)
*A61B 5/339* (2021.01)
(Continued)

(52) U.S. Cl.
CPC .............. *A61B 5/287* (2021.01); *A61B 5/282* (2021.01); *A61B 5/316* (2021.01); *A61B 5/339* (2021.01);
(Continued)

(58) Field of Classification Search
CPC ......... A61B 5/318; A61B 5/363; A61B 5/361; A61B 2576/023
See application file for complete search history.

(56) References Cited

U.S. PATENT DOCUMENTS 5,433,198 A * 7/1995 Desai ................... A61B 5/6852
600/374
5,657,755 A * 8/1997 Desai ................... A61B 5/7445
600/374
(Continued)

FOREIGN PATENT DOCUMENTS

WO WO-2019105986 A1 * 6/2019 ............ A61B 5/316

OTHER PUBLICATIONS

Tobias Weber, Hugo A. Katus, Sebastian Sager, Eberhard P. Scholz, Novel algorithm for accelerated electroanatomic mapping and prediction of earliest activation of focal cardiac arrhythmias using mathematical optimization, Heart Rhythm, vol. 14, Issue 6,2017,pp. 875-882,ISSN 1547-5271, (Year: 2017).*
(Continued)

*Primary Examiner* — Carl H Layno
*Assistant Examiner* — Manolis Pahakis
(74) *Attorney, Agent, or Firm* — Dergosits & Noah LLP; Todd A. Noah

(57) ABSTRACT

A system and method for automatically identifying a location of focal arrhythmogenic activity are provided. The method includes receiving, via a plurality of electrodes in a heart, a collection of acquisitions, each including a set of electrophysiological (EP) signals measured by the electrodes. A respective direction of arrival (DOA) and a respective distance relative to the electrodes from which the set of EP signals originated are estimated for each acquisition. The acquisitions are aggregated, to form a statistical distribution of the acquisitions as a function of estimated DOA and distance. Using a statistical test, it is checked whether the statistical distribution is consistent, in accordance with a predefined consistency criterion. If the statistical distribution is found consistent, an estimated location in the heart of a focal source of an arrhythmogenic activity that generated the
(Continued)

received EP signals is derived from the statistical distribution. The estimated location of the focal source is overlaid on an anatomical map of at least a portion of the heart. The system includes an interface and a processor configured to perform said method.

26 Claims, 17 Drawing Sheets

(51) Int. Cl.
    *A61B 5/282*     (2021.01)
    *A61B 5/316*     (2021.01)
    *A61B 5/361*     (2021.01)
    *A61B 5/318*     (2021.01)
    *A61B 5/363*     (2021.01)
    *A61B 18/14*     (2006.01)

(52) U.S. Cl.
    CPC ............... *A61B 5/318* (2021.01); *A61B 5/361* (2021.01); *A61B 5/363* (2021.01); *A61B 18/1492* (2013.01); *A61B 2576/023* (2013.01)

(56) References Cited

U.S. PATENT DOCUMENTS

| | | | |
|---|---|---|---|
| 6,226,542 B1 | 5/2001 | Reisfeld | |
| 6,301,496 B1 | 10/2001 | Reisfeld | |
| 6,892,091 B1 | 5/2005 | Ben-Haim | |
| 7,536,218 B2 | 5/2009 | Govari | |
| 7,756,576 B2 | 7/2010 | Levin | |
| 8,456,182 B2 | 6/2013 | Bar-Tal | |
| 2002/0010392 A1* | 1/2002 | Desai | A61B 5/743 600/374 |
| 2004/0215238 A1* | 10/2004 | van Dam | A61N 1/3622 607/4 |
| 2004/0243012 A1* | 12/2004 | Ciaccio | A61B 5/349 600/509 |
| 2013/0030257 A1* | 1/2013 | Nakata | G01S 7/003 600/301 |
| 2014/0005562 A1* | 1/2014 | Bunch | A61B 5/316 600/518 |
| 2014/0058294 A1* | 2/2014 | Gross | A61B 8/445 601/2 |
| 2014/0194793 A1* | 7/2014 | Nakata | A61B 5/113 601/48 |
| 2015/0366476 A1 | 12/2015 | Laughner | |
| 2017/0042449 A1 | 2/2017 | Deno | |
| 2017/0079539 A1* | 3/2017 | Chauhan | A61B 5/748 |
| 2017/0172508 A1* | 6/2017 | Huitz | A61B 5/6852 |
| 2017/0202470 A1 | 7/2017 | Urman | |
| 2017/0202471 A1 | 7/2017 | Urman | |
| 2017/0202516 A1* | 7/2017 | Bar-Tal | A61B 5/6852 |
| 2017/0281031 A1 | 10/2017 | Houben | |
| 2018/0296111 A1 | 10/2018 | Deno | |
| 2018/0353084 A1* | 12/2018 | Wainright | A61B 5/318 |
| 2019/0090746 A1* | 3/2019 | Ruppersberg | A61B 5/6852 |
| 2019/0104962 A1* | 4/2019 | Ghoraani | A61B 5/743 |
| 2019/0328256 A1* | 10/2019 | Badie | A61B 5/316 |
| 2019/0328457 A1* | 10/2019 | Villongco | A61B 18/1206 |
| 2020/0221956 A1* | 7/2020 | Tzvieli | G01J 5/0025 |
| 2020/0345261 A1* | 11/2020 | Haeusser | A61B 5/361 |
| 2020/0367751 A1* | 11/2020 | Vandersickel | A61B 5/339 |
| 2021/0059549 A1* | 3/2021 | Urman | A61B 5/6852 |
| 2021/0059550 A1* | 3/2021 | Urman | A61B 5/282 |
| 2021/0138232 A1* | 5/2021 | Paz | A61N 1/36031 |

OTHER PUBLICATIONS

Cantwell, C. D., Roney, C. H., Ng, F. S., Siggers, J. H., Sherwin, S. J., & Peters, N. S. (2015). Techniques for automated local activation time annotation and conduction velocity estimation in cardiac mapping. Computers in biology and medicine, 65, 229-242. .Apr. 27, 2015 (Year: 2015).*

Vogl, Chris & Zheng, Peng & Seslar, Stephen & Aravkin, Aleksandr. (2018). Computer Assisted Localization of a Heart Arrhythmia. (Year: 2018).*

European Search Report for corresponding EPA No. 20191576.6 dated Dec. 7, 2020.

European Search Report for corresponding EPA No. 20192666.4 dated Dec. 23, 2020.

Roney, Caroline H. et al., "An automated algorithm for determining conduction velocity, wavefront direction and origin of focal cardiac arrhythmias using a multipolar catheter", 2014 36th Annual International Conference of the IEEE Engineering in Medicine and Biology Society, Aug. 26, 2014, pp. 1583-1586.

Weber, Frank M. et al., "Wave-Direction and Conduction-Velocity Analysis from Intracardiac Electorgrams—A Single-Shot Technique", IEEE Transactions on Biomedical Engineering, vo. 57, No. 10, Oct. 1, 2010, pp. 2394-2401.

* cited by examiner

AUTOMATIC IDENTIFICATION OF A LOCATION OF FOCAL SOURCE IN ATRIAL FIBRILLATION (AF)

CROSS-REFERENCE TO RELATED APPLICATIONS

This application is related to a U.S. patent application Ser. No. 16/550,734 entitled "Error Estimation of Local Activation Times (LAT) measured by Multiple Electrode Catheter," filed on even date, whose disclosure is incorporated herein by reference.

FIELD OF THE INVENTION

The present invention relates generally to electrophysiological mapping, and particularly to cardiac electrophysiological mapping.

BACKGROUND OF THE INVENTION

Invasive cardiac techniques for mapping electrophysiological (EP) properties of cardiac tissue were previously proposed in the patent literature. For example, U.S. Patent Application Publication 2017/0042449 describes a system and method for local EP characterization of cardiac substrate using multi-electrode catheters. The system selects at least one clique of electrodes from a plurality of electrodes to derive at least one orientation independent signal from the at least one clique of electrodes from the information content corresponding to weighted parts of electrogram signals. The system displays or outputs catheter orientation independent electrophysiologic information to a user or a process.

As another example, U.S. Patent Application Publication 2015/0366476 describes a system and method for mapping the electrical activity of the heart. The system may include a catheter shaft with a plurality of electrodes. A processor of the system may be capable of collecting a set of signals from at least one of the plurality of electrodes. The set of signals may be collected over a time period. The processor may also be capable of calculating at least one propagation vector from the set of signals, generating a data set from the at least one propagation vector, generating a statistical distribution of the data set and generating a visual representation of the statistical distribution, such as a circular histogram of angles. A direction (e.g. propagation angle) and velocity of cellular wavefront propagation may be determined by a comparing the activation times sensed by neighboring electrodes to the target electrode for which the propagation vector is being determined.

U.S. Patent Application Publication 2017/0202470 describes a system and method of identifying focal sources. The method can comprise detecting, via sensors, electrocardiogram (ECG) signals over time, each ECG signal detected via one of the sensors having a location in a heart and indicating electrical activity of the heart, each signal comprising at least an R wave and an S wave; creating an R-S map comprising an R-to-S ratio for each of the ECG signals, the R-to-S ratio comprising a ratio of absolute magnitude of the R wave to absolute magnitude of the S wave; identifying, for each of the ECG signals, local activation times (LATs); and correlating the R-to-S ratios for the ECG signals on the R-S map and the identified LATs and using the correlation to identify the focal sources.

U.S. Patent Application Publication 2017/0281031 describes electroanatomic mapping carried out by inserting a multi-electrode probe into a heart of a living subject, recording electrograms from the electrodes concurrently at respective locations in the heart, delimiting respective activation time intervals in the electrograms, generating a map of electrical propagation waves from the activation time intervals, maximizing coherence of the waves by adjusting local activation times within the activation time intervals of the electrograms, and reporting the adjusted local activation times.

U.S. Patent Application Publication 2004/0243012 describes a method and system for identifying and localizing a reentrant circuit isthmus in a heart of a subject during sinus rhythm. The method may include (a) receiving electrogram signals from the heart during sinus rhythm via electrodes, (b) creating a map based on the electrogram signals, (c) determining, based on the map, a location of the reentrant circuit isthmus in the heart, and (d) displaying the location of the reentrant circuit isthmus.

SUMMARY OF THE INVENTION

An embodiment of the present invention provides a method including receiving, via a plurality of electrodes in a heart, a collection of acquisitions, wherein each acquisition includes a set of electrophysiological (EP) signals measured by the electrodes. A respective direction of arrival (DOA) and a respective distance relative to the electrodes from which the set of EP signals originated are estimated for each of the acquisitions. The acquisitions are aggregated, to form a statistical distribution of the acquisitions as a function of estimated DOA and distance. Using a statistical test, it is checked whether the statistical distribution of the acquisitions is consistent, in accordance with a predefined consistency criterion. If the statistical distribution of the acquisitions is found consistent, an estimated location in the heart of a focal source of an arrhythmogenic activity that generated the received EP signals is derived from the statistical distribution. The estimated location of the focal source is overlaid on an anatomical map of at least a portion of the heart.

In some exemplary embodiments, for a given acquisition, estimating the DOA and distance includes extracting from the set of EP signals in the given acquisition a respective set of relative times of arrival, and estimating the DOA and distance using the extracted relative times of arrival.

In some exemplary embodiments, aggregating the acquisitions includes pre-filtering the acquisitions according to the respective set of relative times of arrival extracted from each acquisition, and including in the statistical distribution of the acquisitions only the pre-filtered acquisitions.

In an exemplary embodiment, pre-filtering the acquisitions according to the extracted set of relative times of arrival includes the steps of: (a) using the estimated DOA and distance, calculating for each acquisition a modeled set of relative times of arrival that would have resulted from an EP wave originating from a focal source at the estimated DOA and distance, and (b) for each acquisition, determining, by applying a predefined geometrical test, a degree of similarity between the extracted set and modeled set of relative times of arrival.

In some exemplary embodiments, estimating the degree of similarity includes calculating a cosine-similarity geometrical test between the two sets. In other embodiments, estimating the degree of similarity includes calculating an estimation error for each relative time of arrival and comparing the estimation error to a given threshold.

In an exemplary embodiment, the method further includes, using the modeled set of relative times of arrival, adjusting time values of annotations over the EP signals for which the voltage-time slope of the EP signal is shallower than a prespecified slope.

In another exemplary embodiment, pre-filtering the acquisitions includes discarding one or more acquisitions determined to have dissimilar sets of times of arrival.

In some exemplary embodiments, deriving the estimated location includes fitting a curve to the statistical distribution and finding a maximum of the curve as a function of estimated DOA and distance.

In some exemplary embodiments, estimating the DOA and the distance includes minimizing a cost-function. In other exemplary embodiments, minimizing the cost-function includes minimizing a weighted cost-function. In further embodiments, minimizing the cost-function includes minimizing the cost-function iteratively, by removing in each iteration an EP signal value having a largest estimation error.

In an exemplary embodiment, deriving the estimated location includes applying k-means analysis to the statistical distribution, projecting estimated locations on anatomy and selecting a location having a projected distance that is less than a given value.

There is additionally provided, in accordance with an exemplary embodiment of the present invention, a system, including an interface and a processor. The interface is configured to receive a collection of acquisitions acquired by a plurality of electrodes in a heart, wherein each acquisition includes a set of electrophysiological (EP) signals. The processor is configured to (a) estimate for each of the acquisitions a respective direction of arrival (DOA) and a respective distance relative to the electrodes, from which the set of EP signals originated, (b) aggregate the acquisitions, to form a statistical distribution of the acquisitions as a function of estimated DOA and distance, (c) check, using a statistical test, whether the statistical distribution of the acquisitions is consistent, in accordance with a predefined consistency criterion, (d) if the statistical distribution of the acquisitions is found consistent, derive from the statistical distribution an estimated location in the heart of a focal source of an arrhythmogenic activity that generated the received EP signals, and (e) overlay the estimated location of the focal source on an anatomical map of at least a portion of the heart.

Another exemplary embodiment of the present invention provides a method including receiving, via a plurality of electrodes in a heart, a collection of acquisitions, wherein each acquisition includes a set of electrophysiological (EP) signals measured by the electrodes. A respective direction of arrival (DOA) and a respective distance relative to the electrodes from which the set of EP signals originated are estimated for at least some of the acquisitions. Based on the estimated DOA and distance, a timing error is estimated in at least an EP signal among the EP signals. A timing of the EP signal is adjusted to fit the estimated DOA and distance and correct the error. An EP map of at least a portion of the heart is generated using the set of EP signals, including the adjusted EP signal.

In some exemplary embodiments, generating the EP map includes generating a local activation times (LAT) map.

In some exemplary embodiments, estimating the DOA and distance includes deriving the DOA and the distance that minimize a cost-function.

In an exemplary embodiment, adjusting the timing of the EP signal includes: (a) selecting an original annotation in the EP signal, (b) determining a corrected annotation, corresponding to the original annotation, based on the estimated DOA and distance, and (c) adjusting the timing of the EP signal upon verifying that the corrected annotation meets a predefined condition.

In another exemplary embodiment, verifying that the corrected annotation meets the predefined condition includes verifying that the corrected annotation falls in a dip between adjacent peaks in the EP signal. In yet another exemplary embodiment, verifying that the corrected annotation meets the predefined condition includes verifying that the corrected annotation and the original annotation lie on a same monotonically-decreasing segment of the EP signal.

In some exemplary embodiments, verifying that the corrected annotation meets the predefined condition includes verifying that the corrected annotation and the original annotation lie on a same monotonic segment of the EP signal, and that a slope of the segment is below a predefined threshold slope.

There is additionally provided, in accordance with an exemplary embodiment of the present invention, a system, including an interface and a processor. The interface is configured to receive a collection of acquisitions acquired by a plurality of electrodes in a heart, wherein each acquisition includes a set of electrophysiological (EP) signals. The processor, configured to: (a) estimate, for at least some of the acquisitions, a respective direction of arrival (DOA) and a respective distance relative to the electrodes from which the set of EP signals originated, (b) based on the estimated DOA and distance, estimate a timing error in at least an EP signal among the EP signals, (c) adjust a timing of the EP signal to fit the estimated DOA and distance and correct the error, and (d) using the set of EP signals, including the adjusted EP signal, generate an EP map of at least a portion of the heart.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
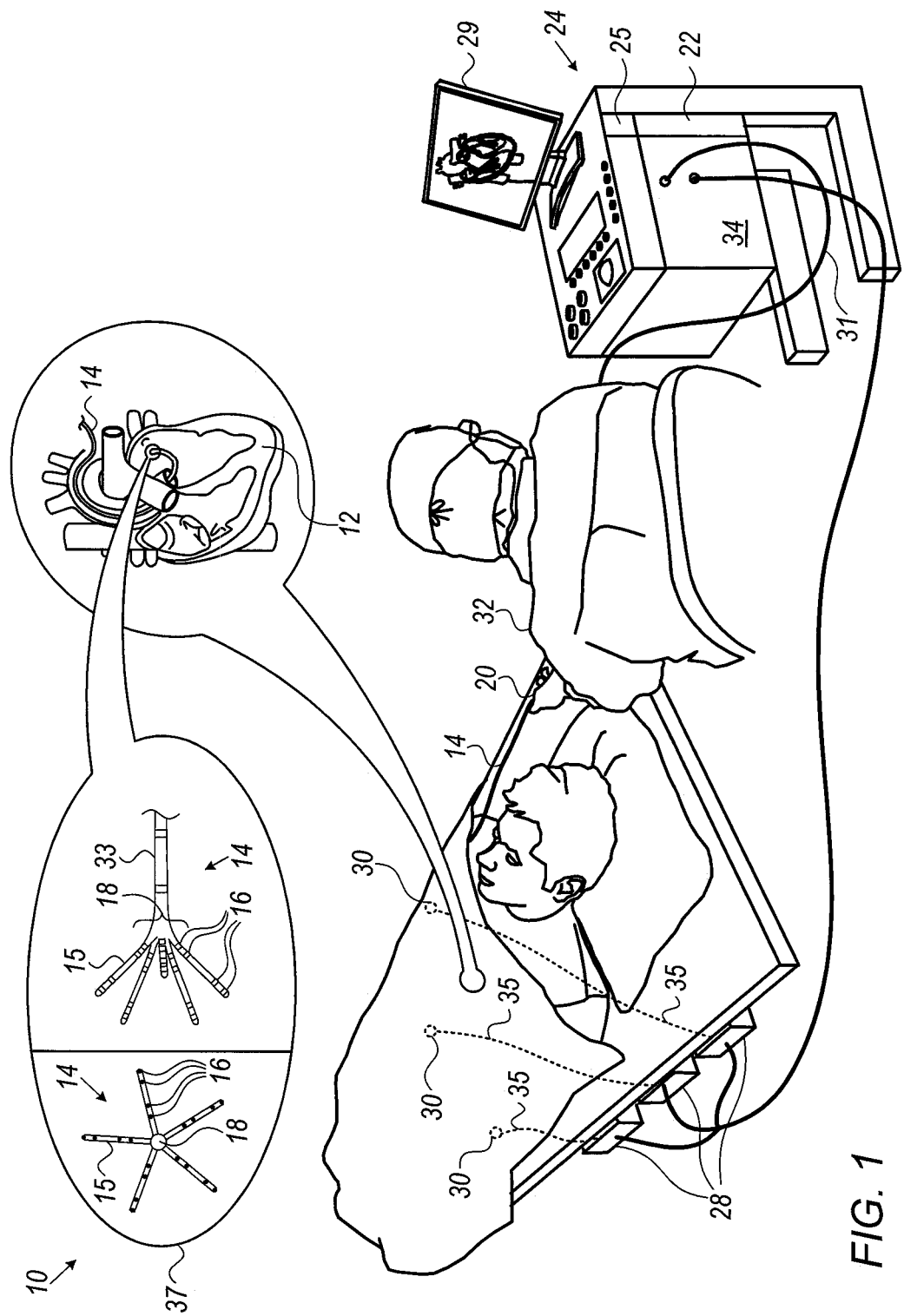
FIG. 1 is a schematic, pictorial illustration of an electrophysiological (EP) mapping system, in accordance with an exemplary embodiment of the present invention.

In an event of a focal type of arrhythmia, an aberrant electrophysiological (EP) wave impulse is abnormally spread from an ectopic focus in the heart. A focal type of arrhythmia may occur due to localized abnormal cardiac tissue that triggers the aberrant EP wave, or by localized abnormal cardiac tissue that forms a small reentry path which causes an erroneous spread of an existing EP wave. In some patients, a localized arrhythmogenic tissue may be ablated to eliminate a focal type of arrhythmia. Therefore, identifying a location of a focal type of arrhythmogenic tissue may be clinically valuable.

Exemplary embodiments of the present invention that are described hereinafter provide EP mapping systems and methods for automatically identifying a location of focal arrhythmogenic activity in the heart. Additionally, or alternatively, some exemplary embodiments provide methods for estimating annotation errors in measured EP values and correcting the annotation errors according to their cause. In some exemplary embodiments, based on a set of annotations that include the corrected annotation, a processor generates an EP map of at least a portion of the heart (e.g., a LAT map).

The EP mapping system uses a multielectrode catheter, such as the Pentaray® catheter (made by Biosense-Webster, Irvine, Calif.), to obtain multiple acquisitions from a cardiac region covered by the electrodes. Each acquisition comprises a set of EP signals measured by the electrodes, with the set sized according to the number of electrodes. However, other multi-electrode catheters may be used, mutatis mutandis, with the disclosed techniques.

In some exemplary embodiments, a processor then estimates, for each acquisition, a direction of arrival (DOA) and a distance, $R_{DOA}$, relative to the electrodes, from which the acquired set of EP signals originated. The processor aggregates the acquisitions to form a statistical distribution (e.g., a histogram, or a cluster map in X-Y space) of the acquisition as a function of estimated DOA and distance, and checks, using a statistical test, whether the statistical distribution of the acquisitions is consistent.

Constancy is checked in accordance with a predefined consistency criterion. Examples of relevant consistency tests include, but are not limited to, constancy estimator or use of confidence interval. As another example, a cluster map in X-Y space may be consistent if one or more clusters in the map contain each at least a given percentage of the data points (e.g., 10%), as described below.

If the statistical distribution of the acquisitions is found consistent, the processor derives from the statistical distribution an estimated location in the heart of a focal source of an arrhythmogenic activity that generated the received EP signals. Finally, the processor overlays the estimated location of the focal source on an anatomical map of at least a portion of the heart.

In some exemplary embodiments, in order to estimate DOA and distance, the processor annotates each EP signal with the time of arrival of an EP wavefront, named hereinafter also as original annotations. The processor extracts from the originally annotated set of signals (i.e., from a given acquisition) a respective set of relative times of arrival. Using a geometrical model, the processor analyzes the extracted set of relative times to indicate the nature of the EP wave in question, as described below. The model assumes that each acquisition is uniquely related to a single travelling broad EP wavefront having a constant velocity over the region in which the EP signals are acquired.

In some exemplary embodiments, when aggregating the acquisitions, the processor pre-filters the acquisitions and includes in the statistical distribution of the acquisitions only the pre-filtered acquisitions. The processor pre-filters the acquisitions by applying the steps of: (a) using the estimated DOA and distance, calculating a modeled set of relative times of arrival, for each acquisition, that would have resulted from an EP wave originating at a focal source having the estimated DOA and distance relative to the catheter, and (b) for each acquisition, applying a test to determine to what degree the extracted set and modeled set of relative times of arrival are similar, and dropping any acquisition that yields dissimilar sets of timings. Examples of relevant tests include a geometrical similarity test, and comparison of estimation errors (also termed hereinafter timing errors) to a given threshold.

In some exemplary embodiments, the geometrical similarity test comprises applying a cosine-similarity geometrical test between the extracted and modeled sets of relative times of arrival. The degree of similarity may range between zero for full dissimilarity to one for full similarity. In an alternative exemplary embodiment, a least square method is used as the geometrical test.

An aberrant EP wave may not necessarily be of focal origin nature, which may be indicated by the similarity check. In an exemplary embodiment, regardless of the nature of the EP wave, i.e., focal or aberrant, the derived modeled relative times may be used to adjust time values of original annotations that are not well defined, i.e., where the voltage-time slope of a wavefront is shallower than a prespecified slope. The adjusted annotations are also referred hereinafter as corrected annotations.

Typically, the processor is programmed in software containing a particular algorithm that enables the processor to conduct each of the processor related steps and functions outlined above.

The disclosed technique for automatically identifying a focal source of an arrhythmogenic activity in the heart may improve the clinical outcome of a related catheter-based treatment of arrhythmia.

System Description

FIG. 1 is a schematic, pictorial illustration of an electrophysiological (EP) mapping system 10, in accordance with an exemplary embodiment of the present invention. System 10 comprises a catheter 14, which is inserted by a physician 32 through the patient's vascular system into a chamber or vascular structure of a heart 12. Physician 32 brings the catheter's distal tip 18 into contact with the heart wall, for example, at an EP mapping target site. Catheter 14 typically comprises a handle 20 which has suitable controls to enable physician 32 to steer, position and orient the distal end of the catheter 14 as desired for the EP mapping.

Catheter 14 is a multi-electrode catheter, such as the aforementioned Pentaray® catheter shown in inset 37. The Pentaray® catheter 14 comprises five flexible arms 15, with each arm carrying four electrodes 16. Thus, a total of twenty EP signals are obtained by system 10 at each instance of EP signal acquisition, as further described in FIG. 2.

Catheter 14 is coupled to console 24, which enables physician 32 to observe and regulate the functions of catheter 14. To aid physician 32, the distal portion of the catheter 14 may contain various sensors, such as contact force sensors (not shown) and a magnetic sensor 33 that provide position, direction, and orientation signals to a processor 22, located in the console 24. Processor 22 may fulfill several processing functions as described below. In particular, electrical signals can be conveyed to and from the heart 12 from electrodes 16 located at or near the distal tip 18 of catheter 14 via cable 31 to console 24. Pacing signals and other control signals may be conveyed from the console 24 through cable 31 and electrodes 16 to the heart 12.

Console 24 includes a monitor 29 driven by processor 22. Signal processing circuits in an electrical interface 34 typically receive, amplify, filter, and digitize signals from the catheter 14, including signals generated by the above noted sensors and the plurality of sensing electrodes 16. The digitized signals are received and used by the console 24 and the positioning system to compute the position and orientation of the catheter 14 and to analyze the EP signals from electrodes 16 as described in further detail below.

During the disclosed procedure, the respective locations of electrodes 16 are tracked. The tracking may be performed, for example, using the CARTO® 3 system, produced by Biosense-Webster. Such a system measures impedances between electrodes 16 and a plurality of external electrodes 30 that are coupled to the body of the patient. For example, three external electrodes 30 may be coupled to the patient's chest, and another three external electrodes may be coupled to the patient's back. (For ease of illustration, only chest electrodes are shown in FIG. 1). Wire connections 35 link the console 24 with body surface electrodes 30 and other components of a positioning sub-system to measure location and orientation coordinates of catheter 14. The method of tracking electrode 16 positions based on electrical signals, named Active Current Location (ACL), is implemented in various medical applications, as, for example, in the aforementioned CARTO®3 system. Details of an ACL subsystem and process are provided in U.S. Pat. No. 8,456,182, which is assigned to the assignee of the present patent application and whose disclosure is incorporated herein by reference.

In some exemplary embodiments, system 10 comprises, in addition to, or instead of, the ACL tracking subsystem, a magnetic position tracking subsystem that determines the position and orientation of magnetic sensor 33, at a distal end of catheter 14, by generating magnetic fields in a predefined working volume and sensing these fields at the catheter, using field generating coils 28. As electrodes 16 have known locations on arms 15, and known relationships to one another, once catheter 14 is tracked magnetically in the heart, the location of each of electrodes 16 in the heart becomes known. A suitable magnetic position tracking subsystem is described in U.S. Pat. Nos. 7,756,576 and 7,536,218, which are assigned to the assignee of the present patent application and whose disclosure is incorporated herein by reference.

Based on the EP signals from electrodes 16 having tracked locations, electrical activation maps may be prepared, according to the methods disclosed in U.S. Pat. Nos. 6,226,542, and 6,301,496, and 6,892,091, which are assigned to the assignee of the present patent application and whose disclosure is incorporated herein by reference.

Processor 22 uses software stored in a memory 25 to operate system 10. The software may be downloaded to processor 22 in electronic form, over a network, for example, or it may, alternatively or additionally, be provided and/or stored on non-transitory tangible media, such as magnetic, optical, or electronic memory. In particular, processor 22 runs a dedicated algorithm as disclosed herein, including in FIG. 2, that enables processor 22 to perform the disclosed steps, as further described below.

The example illustration shown in FIG. 1 is chosen purely for the sake of conceptual clarity. Other types of sensing geometries, such as of a basket catheter or the Lasso® Catheter (produced by Biosense-Webster) may also be employed.

Automatic Identification of a Location of Focal Source in Atrial Fibrillation (AF)

Figure 2:
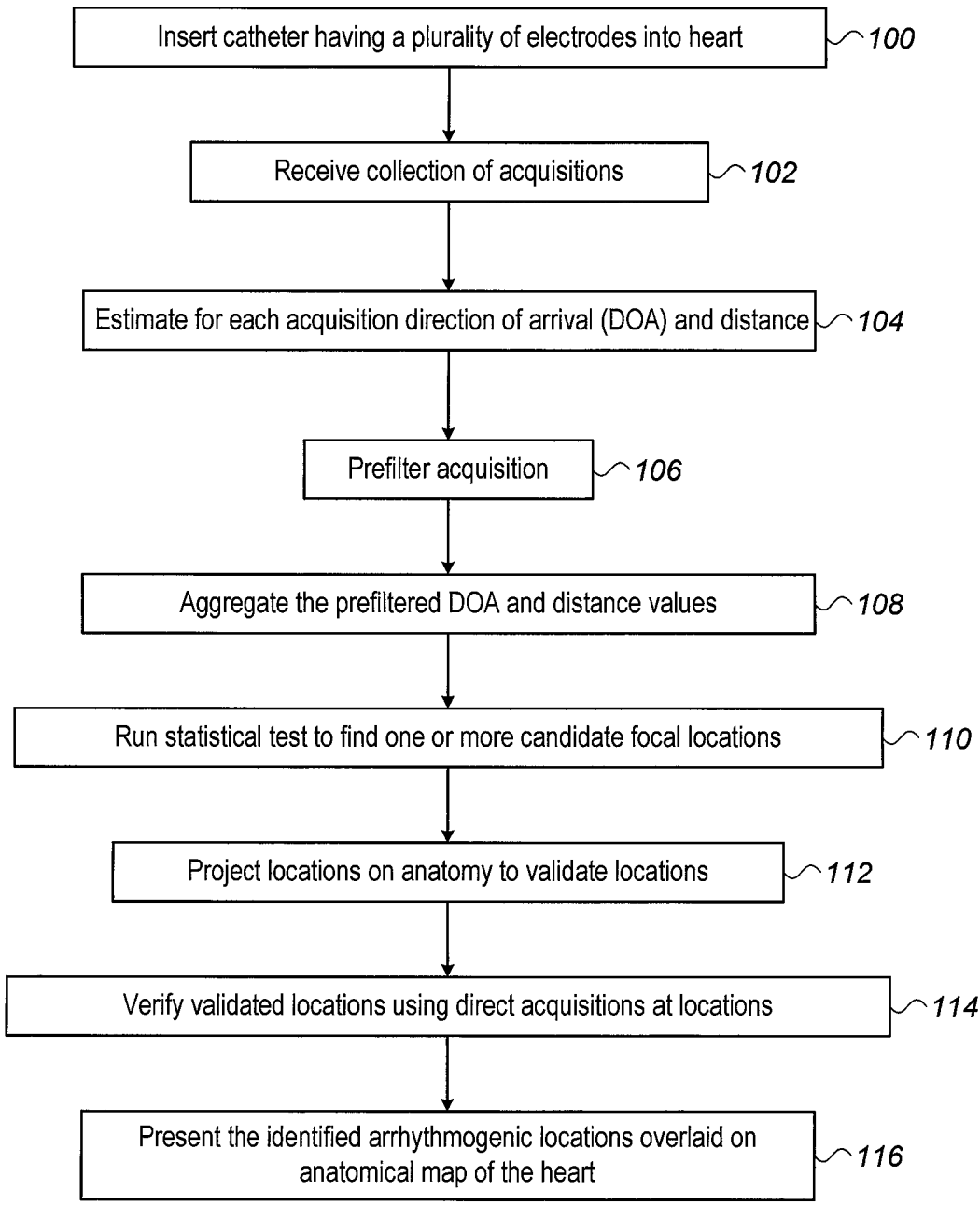
FIG. 2 is a flow chart that schematically illustrates a method for automatic identification of a location of a focal source of arrhythmia, in accordance with an exemplary embodiment of the present invention.

FIG. 2 is a flow chart that schematically illustrates a method for automatic identification of a location of a focal source of arrhythmia, in accordance with an exemplary embodiment of the present invention. The algorithm, according to the presented embodiment, carries out a process that begins with physician 32 inserting catheter 14 having a plurality of sensing electrode 16 into heart 12 of a patient, at a catheter insertion step 100.

Next, system 10 receives a collection of acquisitions of sets of EP signals from electrodes 16 that were brought in contact with cardiac tissue by physician 32, at an EP signals acquisition step 102. In a typical diagnostic interval of thirty seconds used by some of the disclosed embodiments the system collects between 100 and 200 acquisitions comprising ECG segments having each a typical duration of 100-200 mSec. In some exemplary embodiments, an automatic segmentation of the 30 second window is performed by processor 22, so as to produce segments of 100-200 mSec, each segment corresponds to a single activation propagating through the atria.

Next, processor 22 derives from each acquisition estimated values of DOA and distance of a presumed focal source, at a DOA derivation step 104. Processor 22 then prefilters each acquisition to drop acquisitions not suitable for inclusion in subsequent statistical analysis, at a prefiltration step 106. In some exemplary embodiments, processor 22 prefilters the acquisition by comparing errors in estimated relative times between extracted EP values and modeled EP values. This stage may include attempting further processing, such as including iterative calculation to improve DOA estimation and thereby reduce estimation errors, as described below.

In other exemplary embodiments, the processor prefilters the acquisition by running a geometrical test of the consistency of modeled EP values and the extracted EP values (e.g., running cosine-similarity test).

Either way, at an aggregation step 108, processor 22 aggregates the verified DOA and distance values. Next processor 22 runs a statistical test to find one or more candidates of DOA and distance (i.e., candidate focal locations), if such exist, at a statistical analysis step 110.

The processor verifies if and which of the candidate locations is a valid location, by projecting the location on the anatomy, at a projection validation step 112.

Furthermore, the processor verifies for validated candidate location that at least a minimal number of focal indicative ECG signals, described below, were acquired at the validated location, at a direct validation step 114.

Finally, at a focal source presenting step 116, processor 22 overlays the one or more identified locations of a focal source of arrhythmogenic activation an anatomical map of at least a portion of heart 12.

The exemplary flow chart shown in FIG. 2 is chosen purely for the sake of conceptual clarity. More details and specific embodiments of the steps described briefly above are brought below, including in flowcharts of FIGS. 5 and 6.

Figure 3A:
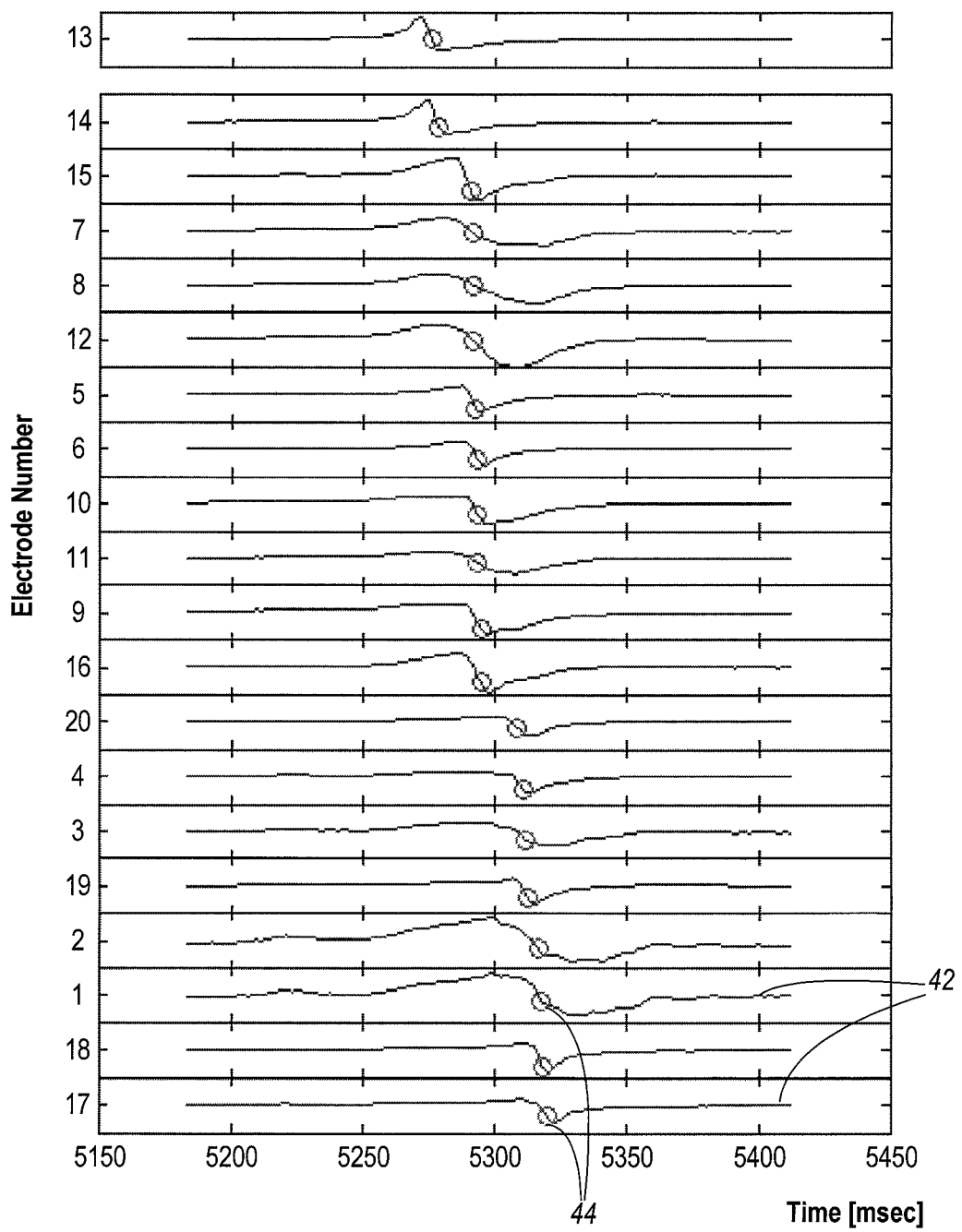
FIGS. 3A and 3B are two plots showing graphs of EP signals that were acquired by the system of FIG. 1, in accordance with an exemplary embodiment of the present invention.
Figure 3B:
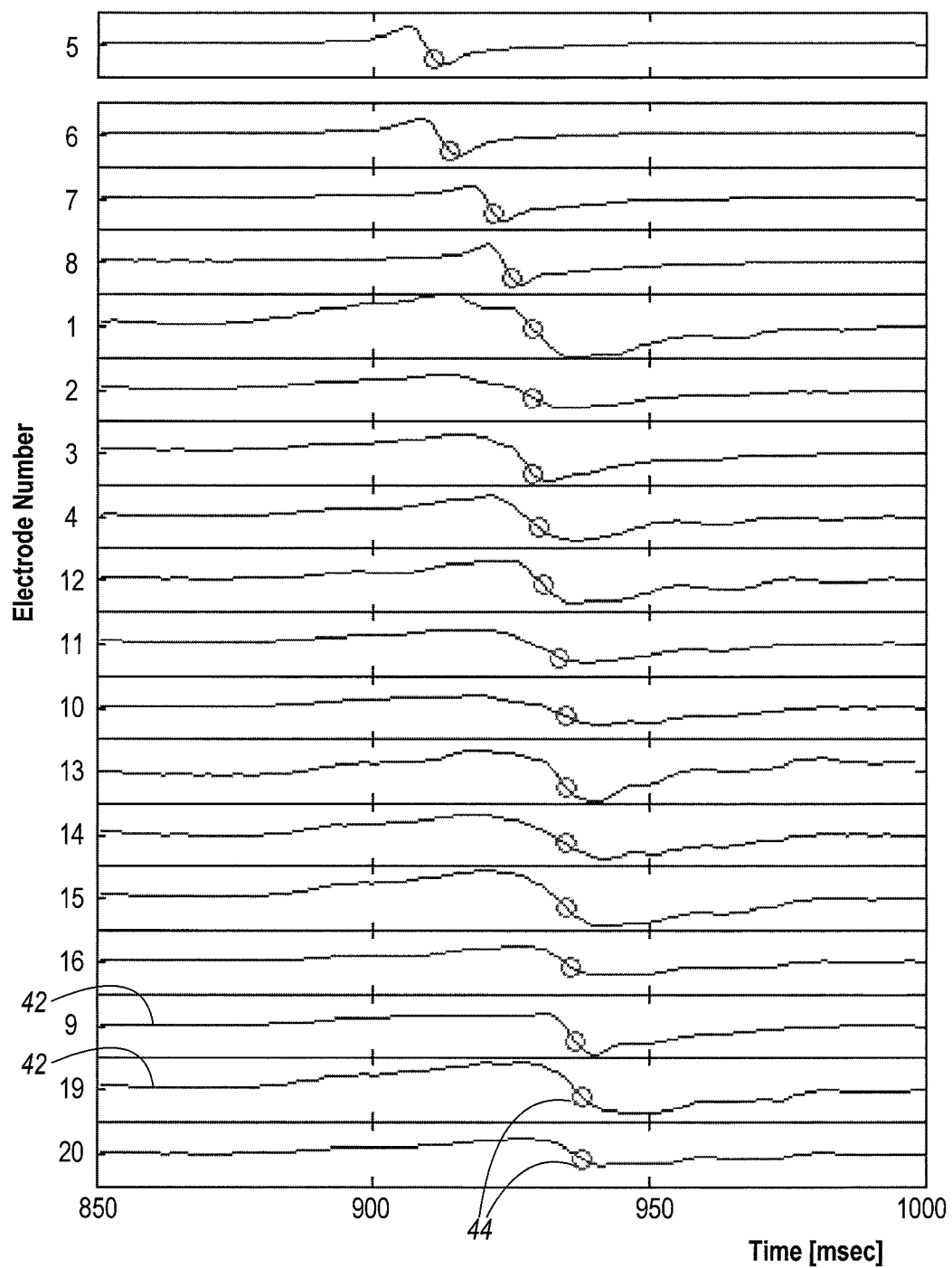

Direction of Arrival (DOA) and Distance Derivation and Verification by a First Method FIGS. 3A and 3B are two plots showing graphs 42 of EP signals that were acquired by the system of FIG. 1, in accordance with an exemplary embodiment of the present invention. The shown EP signals were acquired, for example, by the EP mapping system of FIG. 1 using catheter 14. The two acquisition are part of multiple acquisitions, numbered between several tens and several hundred. Such a collection may include acquisitions taken at different intracardiac placements of the catheter and/or repeated acquisitions taken during the same placement. Using the tracking system, each of the plurality of electrodes has a location in the heart.

The graphs show originally annotated times 44 at which the EP wave "strikes" each of the twenty electrodes of catheter 14. The annotations are made by a method known in the art, such as described in U.S. Pat. No. 8,700,136, which is assigned to the assignee of the present patent application and whose disclosure is incorporated herein by reference.

In FIG. 3A, the EP wave first strikes electrodes "13" and "14", then electrodes "15" and "7" and so on. In FIG. 3B, the EP wave first strikes electrodes "5" and "6", then electrodes "7" and "8" and so on.

As seen in FIGS. 3A and 3B, some of the voltage-time slopes of the EP signal that are originally annotated are not well defined, i.e., are shallow (for example, in graphs 10 and 11 of FIG. 3B). In an exemplary embodiment, the disclosed technique improves the accuracy of such annotations, by deriving corrected annotations, as shown below in FIGS. 7A, 8A and 9A, even if a focal source of arrhythmogenic activity is not identified by the technique. In an exemplary embodiment, modeled times that are derived below, which are based on the known geometry of catheter 14, are used to adjust time values of original annotations that are not well defined, i.e., where the voltage-time slope seen in FIGS. 3A and 3B is shallower than a prespecified slope.

FIGS. 3A and 3B are brought by way of example. If another catheter having multiple electrodes is used, such as basket or Lasso® catheters, the size of acquisition (e.g., number of graphs in a set) and the annotated times will reflect the geometry of the given catheter, while similarly used by the disclosed technique.

Figure 4A:
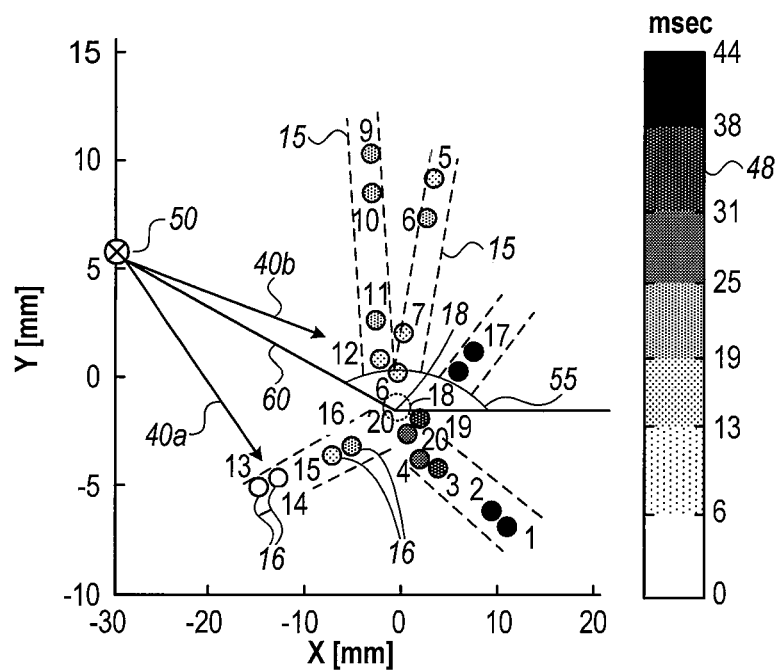
FIGS. 4A and 4B are plots showing relative arrival times extracted and modeled using EP signals of graphs of FIGS. 3A and 3B, respectively, in accordance with an exemplary embodiment of the present invention.
Figure 4A:
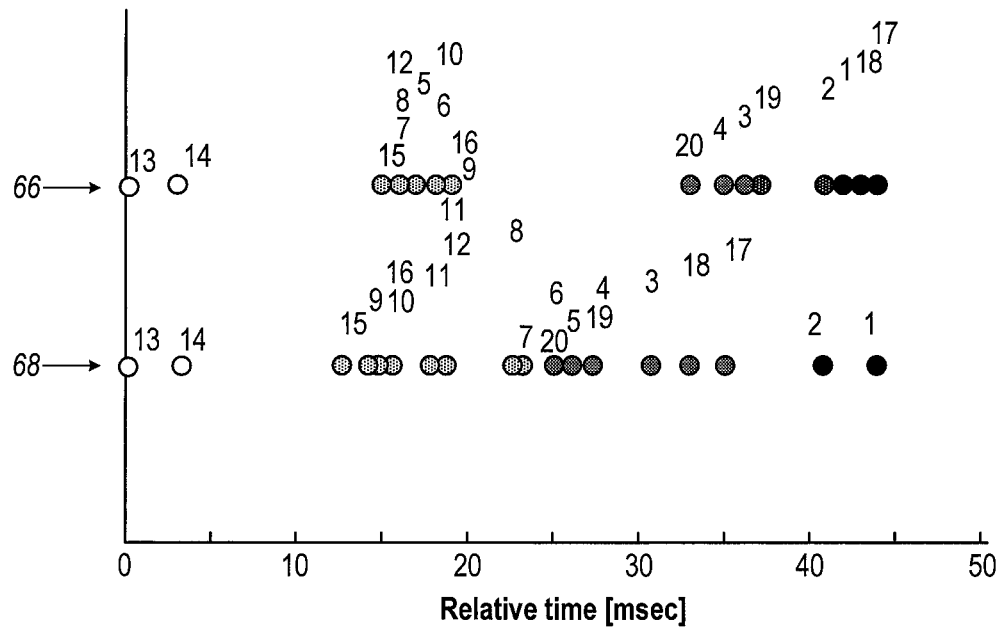
Figure 4B:
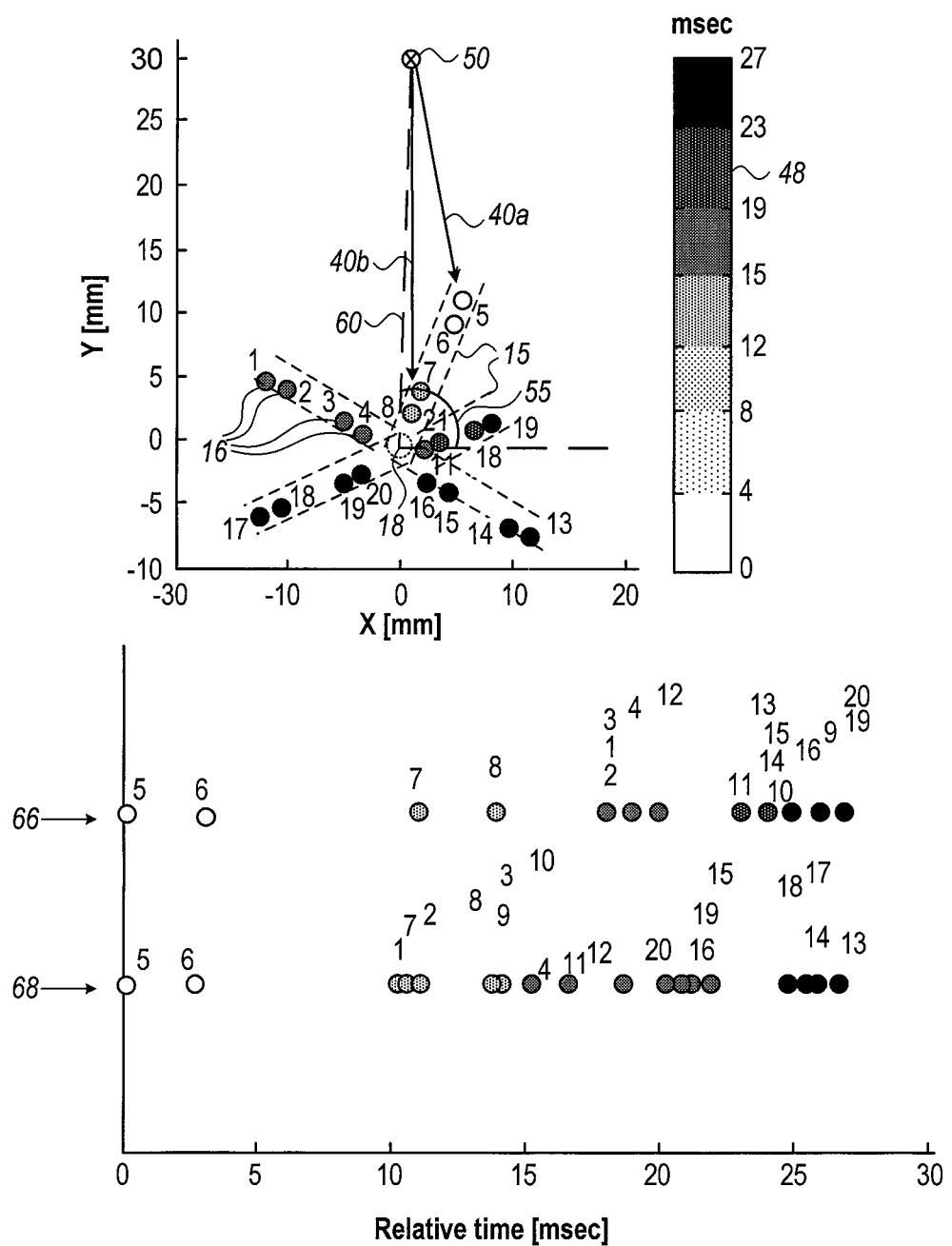

FIGS. 4A and 4B are plots showing relative arrival times extracted and modeled using EP signals of graphs of FIGS. 3A and 3B, respectively, in accordance with an embodiment of the present invention. Processor 22 will pre-filter the acquisitions according to respective extracted set of relative times of arrival by performing the steps described below.

Extracted times 66 in FIGS. 4A and 4B are derived by processor 22 calculating time differences between original annotated times 44 of FIGS. 3A and 3B, respectively. Respective modeled relative times 68 in FIGS. 4A and 4B are subsequently derived by processor 22, using corrected annotated times (not shown, as described below).

A color scale 48 in the upper part of FIGS. 4A and 4B, encodes the relative times of arrival by color encoding each of the depicted twenty electrodes 16 of catheter 14. The upper part of FIGS. 4A and 4B further shows the tracked positions of electrodes 16 (over schematically demarked arms 15 of Pentaray® catheter 14) at the two instances where the electrodes acquired the EP signals. The position of each electrode 16 in 3D space is tracked using, for example, the aforementioned ACL tracking technique. The X-Y-Z axis (Z not shown) belong to a fixed reference axial system, such as of position tracking system applying the ACL method.

Based on extracted relative times of arrival 66, processor 22 estimates geometrically (e.g., as indicated by arrows 40a and 40b) a presumed focal source 50 from which the EP wave appears to come, as further marked by a distance indicated by line 60 that connects the common location at which arrows 40a and 40b originate from distal tip 18 of catheter 14.

The lower part of FIGS. 4A and 4B shows on the same graph set of extracted relative times of arrival 66, and the respective modeled set relative times of arrival 68. Relative times of arrival 66 are derived by processor 22 from the originally annotated times at which the actual EP wave "strikes" the electrodes. Modeled times 68 are calculated by processor 22 using estimated DOA 55 and distance 60, assuming a simulated EP wave originating at a focal source 50 having the estimated DOA and distance relative to electrodes 16.

In an exemplary embodiment, an acquisition is determined indicative of a focal source by the processor only if a cosine-similarity timings match derived from the acquisition exceeds a value of 0.9. Geometrical test (e.g., metrics) other than cosine-similarity that check to what degree the extracted and modeled sets are similar, such as the Hamming-distance, may be used.

The processor estimates to what degree each pair of such sets per acquisition, marked herein as vectors $S_{EX}$ and $S_{MD}$, are similar using the cosine-similarity equation:

$$\text{Cosine Similarity} = \frac{S_{EX} \cdot S_{MD}}{\|S_{EX}\| \|SS_{MD}\|} \qquad \text{Eq. 1}$$

Cosine-similarity, in which a normalized inner product of the two ordered sets is calculated, may give any value between −1 and 1. Practically, the cosine-similarity is particularly used in positive space, where the outcome is bound within [0, 1). For example, a value of 1 corresponds to full similarity, whereas a value of zero, or any negative value, indicates full dissimilarity. In an exemplary embodiment, if the calculated cosine-similarity gives a value above a prespecified minimum value, such as above 0.9, the processor determines the sets to be similar.

Processor 22 runs the similarity check over all the sets derived from the collection of acquisitions, and drops acquisitions having cosine-similarity below the prespecified minimum value (e.g., <0.9).

Next, processor 22 calculates, only for acquisition that successfully passed the Cosine similarity test, a direction of arrival (DOA) 55, defined as the phase of vector ($r_{50}$-$r_{18}$), and distance 60 from which the set of signals originated using equations 2 and 3:

$$DOA = \text{phase}(r_{50}-r_{18}) \quad \text{Eq. 2}$$

$$\text{Distance} = \|r_{50}-r_{18}\|, \quad \text{Eq. 3}$$

where $r_{50}$ and $r_{18}$ are the vector coordinates of the presumed focal source 50 and of catheter's 14 distal tip 18, respectively. In some embodiments, when converting the system coordinates from 3D to 2D, $r_{18}$ will be zero vector, since the center of the catheter is placed at the origin of the XY space.

Figure 5:
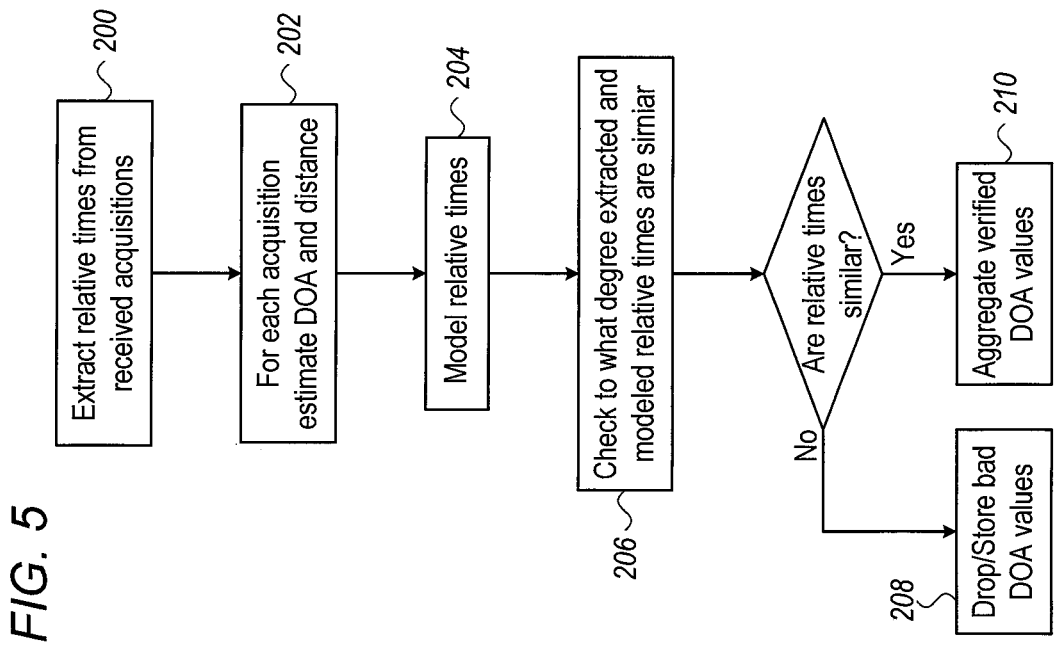
FIG. 5 is a flow chart that schematically illustrates a method for deriving direction of arrival (DOA) and distance along the steps illustrated in FIGS. 4A and 4B, in accordance with an exemplary embodiment of the present invention.

FIG. 5 is a flow chart that schematically illustrates a method for deriving direction of arrival (DOA) and distance along the steps illustrated in FIGS. 4A and 4B, in accordance with an exemplary embodiment of the present invention. The process begins with processor 22 extracting relative times of arrival 66 from the originally annotated EP signals, at a relative times extraction step 200.

Next, based on the assumptions that the EP signals were generated by (a) a single EP wave having a broad wavefront that (b) propagates at a constant velocity, and based on the known geometry of catheter 14, processor 22 derives per acquisition estimated values of DOA 55 and distance 60 of the EP wave, at a DOA and distance estimation step 202.

Next, based on the estimated DOA 55 and distance 60 values, processor 22 calculates relative times that a focal wave having the tentative DOA and distance from step 106 would have generated, at a relative times modeling step 204. Processor 22 then checks, for example by using a cosine-similarity test, to what degree the extracted and modeled sets of relative times are similar, at a similarity checking step 206.

If the sets are found dissimilar, processor 22 stores or drops the bad DOA and distance values as being non-indicative, at an acquisition dropping step 208. All acquisitions having sets of extracted and modeled relative times that are found similar (i.e., passed prefiltration) are aggregated by processor 22 into separate distributions as a function of DOA and distance (e.g., into histograms 70 and 72 of FIGS. 11A and 11B below), at an aggregation step 210. As shown below in FIGS. 11A and 11B, the aggregated DOA and distance are statistically analyzed to find a location of a focal source, if one deemed by the histograms to exist.

The exemplary flow chart shown in FIG. 5 is chosen purely for the sake of conceptual clarity. Additional steps may be typically performed, such as physician 32 initially anatomically mapping relevant parts of heart 12 (e.g., using fast anatomical mapping (FAM) procedure) to obtain an anatomical map. The criteria may vary with the type of statistical tools used. In an exemplary embodiment, dropped sets of modeled timings may still be used for adjusting respective originally annotated times that are not well defined, as described below under "LAT improvements."

Figure 6:
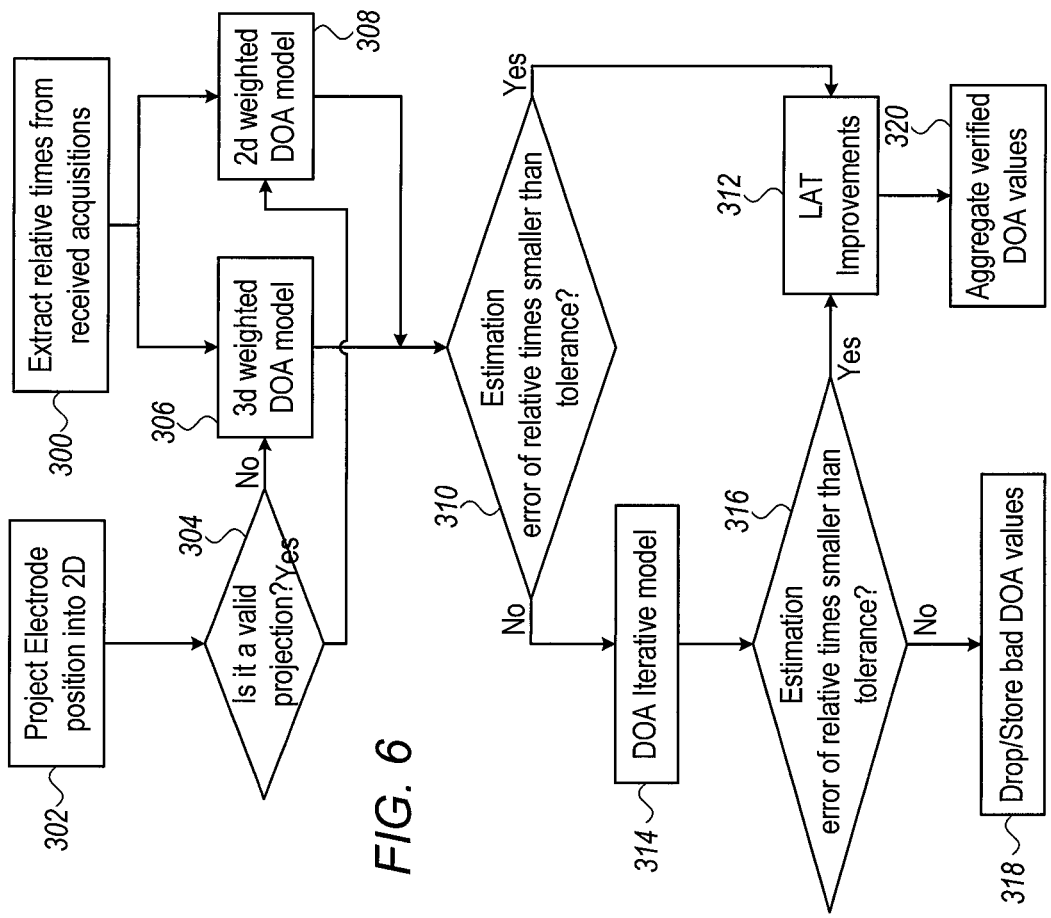
FIG. 6 is a flow chart that schematically illustrates a method for deriving direction of arrival (DOA) from a focal source, in accordance with another exemplary embodiment of the present invention.

Direction of Arrival (DOA) and Distance
Derivation and Verification by a Second Method FIG. 6 is a flow chart that schematically illustrates a method for deriving direction of arrival (DOA) from a focal source, in accordance with another exemplary embodiment of the present invention.

The process shown in FIG. 6 begins with processor 22 extracting relative times of arrival 66 from the originally annotated EP signals, at a relative times extraction step 300.

Next, the algorithm checks whether to apply a 3D or 2D weighted DOA model estimation, by checking whether projecting (i.e., projection step 302) the catheter into a 2D space is valid, as described below, at a projection checking step 304.

Next, depending on whether projection step 304 was found an invalid step or a valid step, processor 22 runs a 3D weighted DOA finding model, at a 3D modeling step 306, or a 2D weighted DOA finding model, at a 2D modeling step 308, respectively.

Either using 3D or 2D models, processor 22 than checks if estimated errors between modeled and extracted relative times are lower than a given threshold, at an estimation error step 310.

If estimation errors are within the given threshold, processor 22 applies a LAT improvement calculation, to make DOA estimation more accurate, at a LAT improvements step 312. LAT improvements are further described below.

If, on the other hand, estimation errors are higher than the given threshold, processor 22 runs a DOA iterative model, at a DOA iterative estimation step 314.

At a follow up estimation error step 316, processor 22 than checks if estimation errors recalculated using the iterative model are lower than the given threshold. If not, processor 22 stores or drops the bad DOA and distance values as being non-indicative, at an acquisition dropping step 318. If, however, the iterative model was successful, processor 22 apply LAT improvements step 312 to the results.

Either way, LAT improved estimates of successfully prefiltered DOA and distance are aggregated by processor 22, at an aggregation step 320. As shown below, the aggregated DOA values are statistically analyzed to find one or more location of a focal source, if ones deemed by the statistical model to exist.

Figure 7A:
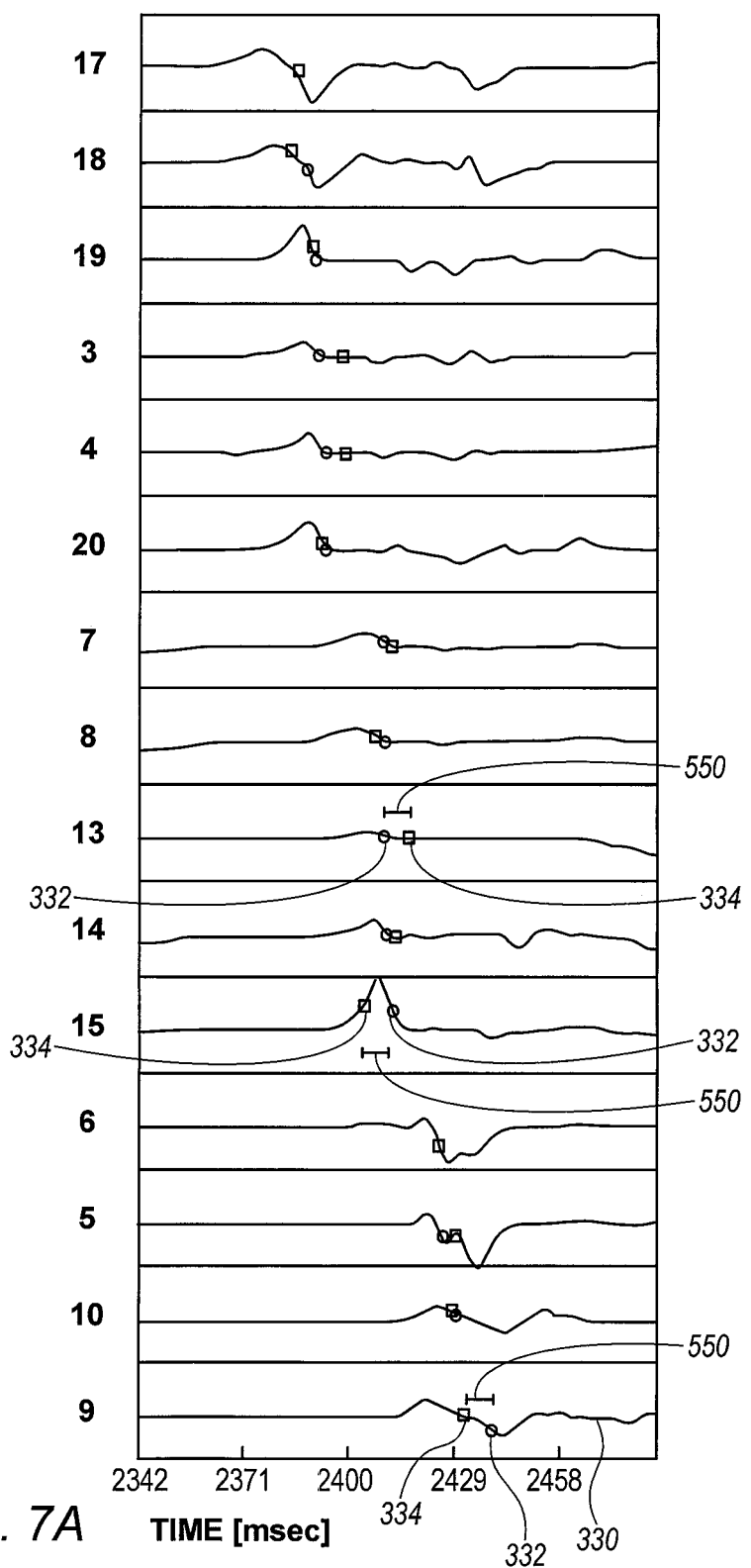
FIGS. 7A-7C are, respectively, (a) a plot showing graphs of unipolar EP signals that were acquired by the system of FIG. 1, (b) the location of the catheter, and (c) an isochronal map showing respective estimation errors in extracted EP values, in accordance with an exemplary embodiment of the present invention.
Figure 7B:
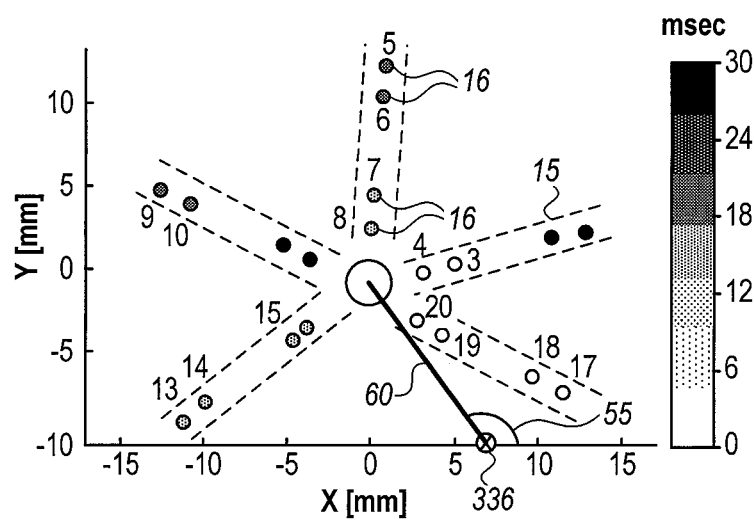
Figure 7B:
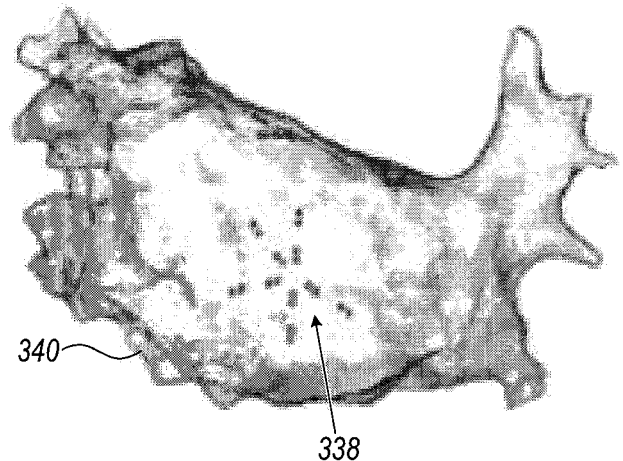
Figure 7C:
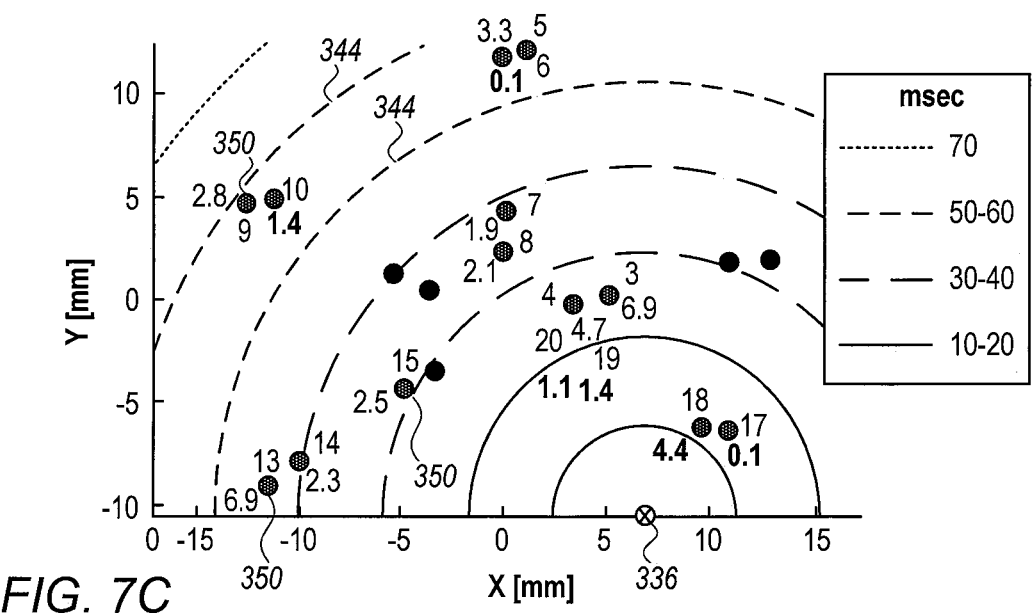

In an exemplary embodiment, the disclosed method described in FIG. 6 for deriving DOA and direction utilizes a cost function in 3D space, as described in FIGS. 7A-7C.

FIGS. 7A-7C are, respectively, (a) a plot showing graphs of unipolar EP signals that were acquired by the system of FIG. 1, (b) the location of catheter 14, and (c) an isochronal map showing respective estimation errors 550 in extracted EP values, in accordance with an exemplary embodiment of the present invention. Specifically, FIG. 7B shows the location of distal tip 18 of catheter 14 catheter 14 in X-Y space, and an actual location 338 of the catheter on the anatomy of left atria 340.

Figure 8A:
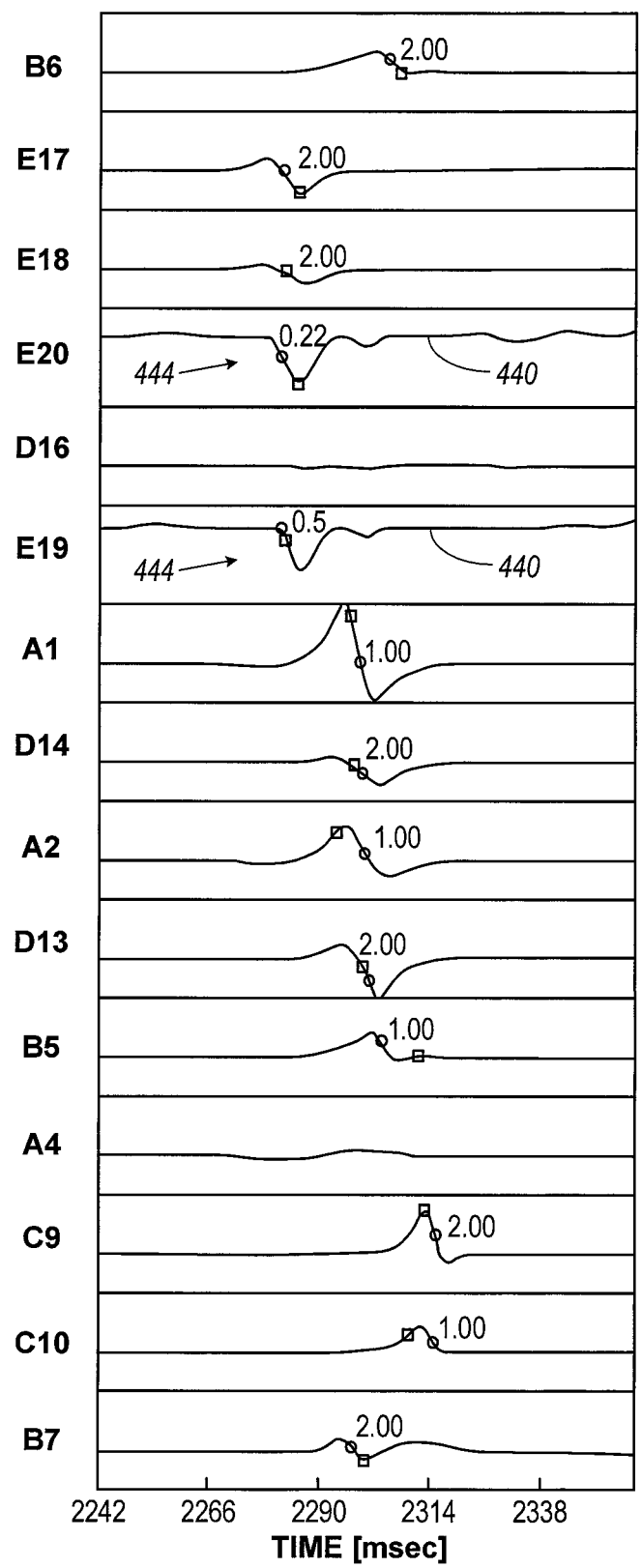
FIGS. 8A and 8B are, respectively, a plot showing graphs of unipolar EP signals that were acquired by the system of FIG. 1, and an isochronal map showing respective estimation errors in extracted EP values, in accordance with an exemplary embodiment of the present invention.
Figure 9A:
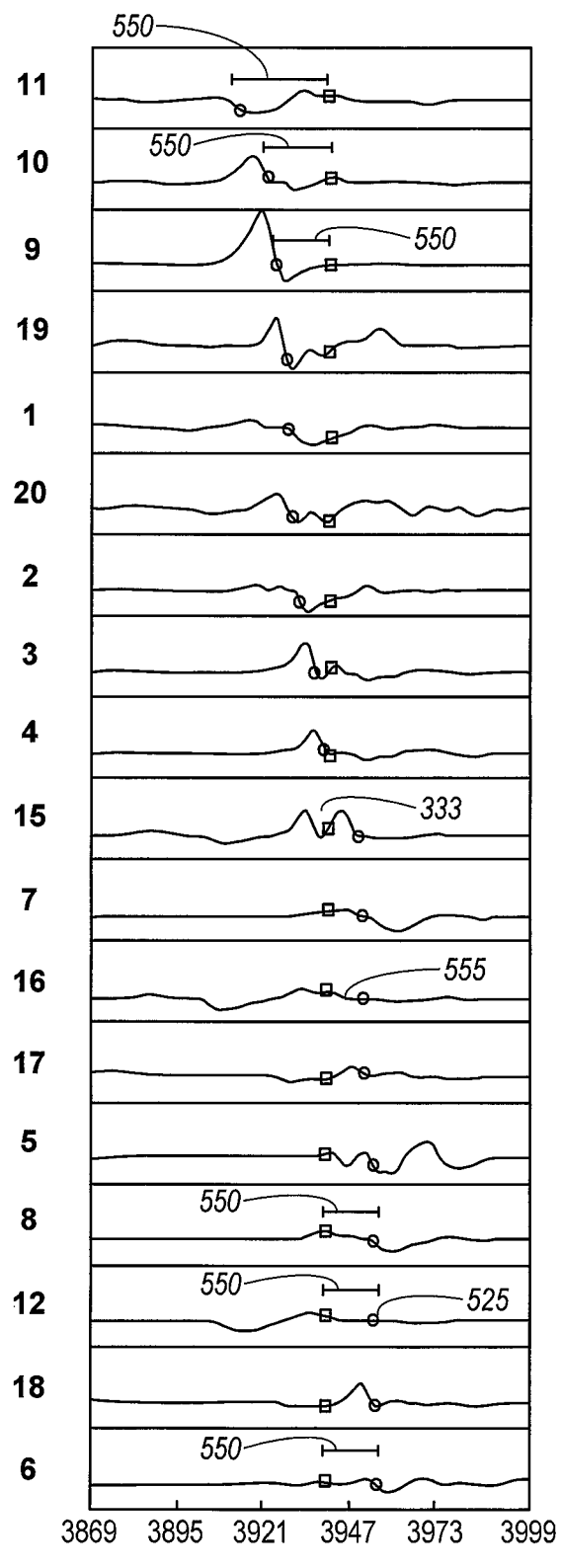
FIGS. 9A and 9B are, respectively, a plot showing graphs of unipolar EP signals comprising estimation errors higher than a given threshold, and an initially estimated location of the focal source in X-Y space, in accordance with an exemplary embodiment of the present invention.

Estimation errors 550 (i.e., timing errors 550) are shown in FIGS. 7A, 8A and 9A, as time differences between original annotations and corrected annotations.

FIG. 7A shows a set of unipolar signals 330 with measured and originally annotated local activation time 332 ($t_i$—circles) and corresponding estimated local activation times 334 ($\tilde{t}_i$—squares), i.e., corrected annotations, that were derived using a cost-function model described below. Estimated errors 550 between measured and modeled EP values of activation times are calculated for each electrode as the time differences $\tilde{t}_i - t_i$, as further described below.

The cost-function based model of DOA is applied for each acquisition comprising a set of at least 10 local atrial activation, $t_i$, the time of local atrial activity of the i electrode, $i=1, \ldots, m$ $10 \le m \le N$, where N is the number of valid electrodes of the catheter, e.g. N=20 for PentaRay® catheter. If a single EP wave is assumed to originate from any point in 3D space and to travel toward the catheter with a constant conduction velocity (CV) then a cost-function $J(\theta)$ can be defined for the "total cost" of the model:

$$J(\theta) = \frac{1}{m}\sum_{i=1}^{m}(vd_i + t_0 - t_i)^2 + \frac{\lambda}{2m}\left(x_0^2 + y_0^2 + z_0^2 + \frac{1}{v^2}\right) \quad \text{Eq. 4}$$

In Eq. 4, $d_i = \sqrt{(x_i-x_0)^2+(y_i-y_0)^2+(z_i-z_0)^2}$, is defined as the distance from a DOA point located at $(x_0, y_0, z_0)$ and arriving at $t_0$ to the i electrode located at $(x_i, y_i, z_i)$. Time $t_0$ is defined as the bias time of arrival for all electrodes and $v$ is 1/CV of the wave. The term $$\frac{\lambda}{2m}\left(x_0^2 + y_0^2 + z_0^2 + \frac{1}{v^2}\right)$$

in $J(\theta)$ is a regularization term and it effectively gives preference to a solution that are closer to the distal tip 18 of the catheter and thus increases the probability to find solutions within the anatomy of the atria. The purpose of our model is to minimize the cost $J(\theta)$ by finding the "best" $\theta=(x_0, y_0, z_0, t_0, v)$, that minimizing the cost $J(\theta)$, this could be done using a gradient descent estimation procedure with a constraint that, $v$ is greater than zero. Gradient descent is based on the observation that if the multi-variable function $J(\theta_k)$ at the k'th iteration is defined and differentiable in a neighborhood of a point $\theta_k$ then $J(\theta_k)$ decreases fastest if one goes from $\theta_k$ in the direction of the negative gradient of $J(\theta_k)$, such that $\theta_{k+1}=\theta_k-\gamma\cdot\nabla(\theta_k)$ and $\nabla$ represents the differential operation and $\gamma$ is the learning rate factor. $\gamma$ should be small to ensure conversion but not too small to overcome slow conversion or convergence to a local minimum of $J(\theta)$. For formal description of gradient descent algorithm, we derive the differential equation of $J(\theta)$ with respect to each one of the parameters $(x_0, y_0, z_0, t_0, v)$:

$$\frac{\partial J(\theta)}{\partial x_0} = -\frac{2}{m}\sum_{i=1}^{m}\frac{(v\cdot d_i + t_0 - t_i)}{d_i}(x_i - x_0) + \frac{\lambda\cdot x_0}{m} \quad \text{Eq. 5}$$

$$\frac{\partial J(\theta)}{\partial y_0} = -\frac{2}{m}\sum_{i=1}^{m}\frac{(v\cdot d_i + t_0 - t_i)}{d_i}(y_i - y_0) + \frac{\lambda\cdot y_0}{m}$$

$$\frac{\partial J(\theta)}{\partial z_0} = -\frac{2}{m}\sum_{i=1}^{m}\frac{(v\cdot d_i + t_0 - t_i)}{d_i}(z_i - z_0) + \frac{\lambda\cdot z_0}{m}$$

$$\frac{\partial J(\theta)}{\partial v} = \frac{2}{m}\sum_{i=1}^{m}(v\cdot d_i + t_0 - t_i)\cdot d_i + \frac{\lambda}{m\cdot v^3}$$

$$\frac{\partial J(\theta)}{\partial t_0} = \frac{2}{m}\sum_{i=1}^{m}(v\cdot d_i + t_0 - t_i)$$

The upper illustration of FIG. 7B depicts the resulting estimated focal activity. In FIG. 7B, a color scale (same as scale 48 in FIGS. 4A and 4B) encodes the relative times of arrival by color encoding each of the depicted twenty electrodes 16 of catheter 14. FIG. 7B further shows the tracked positions of electrodes 16 (over schematically demarked arms 15 of Pentaray® catheter 14) at two separate instances where the electrodes acquired the EP signals. The position of each electrode 16 in 3D space is tracked using, for example, the aforementioned ACL tracking technique. The X-Y-Z axis (Z not shown) belong to a fixed reference axial system, such as of position tracking system 20 applying the ACL method.

Finally, also shown are the cost-function model derived DOA 55 and distance 60 from which the set of signals 330 originated.

FIG. 7C (the isochronal map) shows that the analyzed EP wave is propagating from a focal source location 336 inside circle lines 344 that represent time of arrival in milliseconds according to the color-bar in the right-hand side of FIG. 7C. Circles 350 represent location of electrodes with the number within the circle represents the cost-function derived individual (i.e., per electrode) estimation errors 550 of FIG. 7A in milliseconds.

LAT Improvements

In some exemplary embodiments of the present invention, a processor adjusts the originally annotated times of an EP signal by selecting an original annotation in the EP signal, determining a corrected annotation, corresponding to the original annotation, based on the estimated DOA and distance, and adjusting the timing of the EP signal upon verifying that the corrected annotation meets a predefined condition, as described below.

Estimation errors 550 are derived (e.g., calculated) by processor 22 by calculating (a) impinging times $\tilde{t}_i$ using the cost function minimizing set of location and conduction velocity, $\theta=(x_0, y_0, z_0, t_0, v)$, and the measured location of the electrodes, and (b) calculating the difference $\tilde{t}_i-t_i$ per electrode.

In an embodiment, a LAT value $t_i$ is replaced by $\tilde{t}_i$ to improve LAT estimation if one of the predefined conditions 1-3 are met:

1. $\tilde{t}_i$ is found within a fractionated signal (not shown) or double potential LAT (such as value 333 of the EP signal of electrode 15 in FIG. 9A).

2. $\tilde{t}_i$ is not an anchor, meaning the weight of the LAT, as described in the weighted model below (Eq. 6), is less than 0.3. LAT with low weights are LATs with "shallow" deflections in voltage (i.e., voltage-time slope of the EP signal is shallower than a prespecified slope) and therefore their originally annotated time, such as original annotation 525 in FIG. 9A, is less "reliable".

3. $t_i$ and $\tilde{t}_i$ lay both between start and end points of unipolar negative deflection (such as negative deflection 555 of the EP signal of electrode 16 in FIG. 9A).

The description continues to another subject, describing a simplified implementation of the cost function.

In some exemplary embodiments, a cost function in 2D space can be applied. In the 2D model, the catheter is projected to a surface; this is performed by taking the two eigen vectors with highest eigen values. If the energy preserved by the two eigen vectors is greater than 95% than the model assumes that the projection from 3D space to a surface is valid and the set of equation is simpler, $=(x_0, y_0, t_0, v)$ without the z dimension.

Figure 8B:
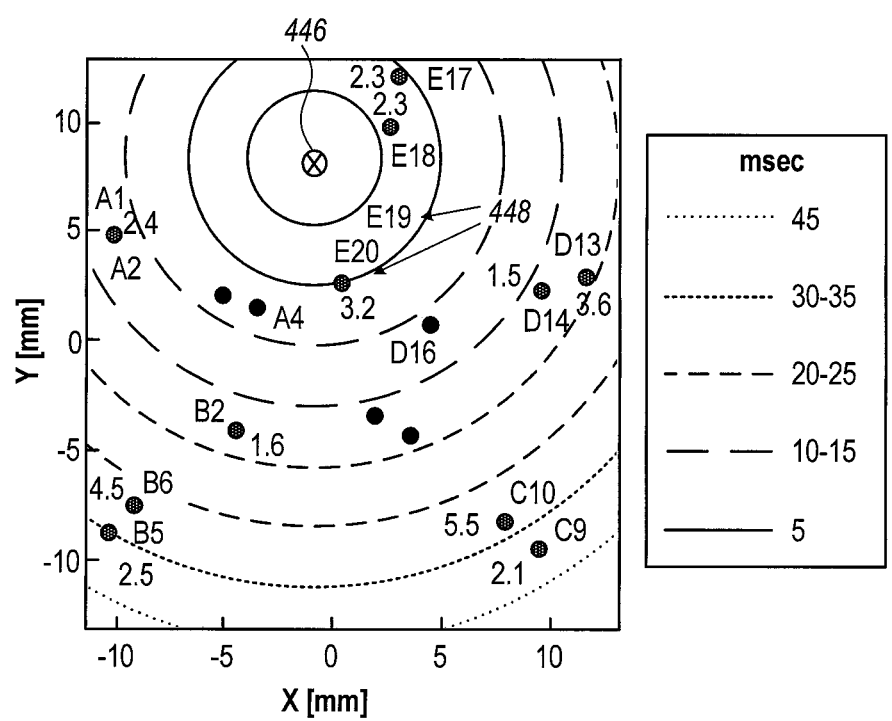

In some exemplary embodiments, an alternative DOA estimation step, comprising estimating the DOA using a weighed cost-fiction, is used by the algorithm, and is described in FIGS. 8A and 8B.

FIGS. 8A and 8B are, respectively, a plot showing of graphs of unipolar EP signals 440 that were acquired by the system of FIG. 1, and an isochronal map showing respective estimation errors in extracted EP values, in accordance with an exemplary embodiment of the present invention. The main concept behind the weighted cost-function DOA model described below is that "sharp" activation is more "reliable" than a shallow activation, where the level of sharpness is defined based dv/dt of the unipolar signal at $t_i$. Each $t_i$ is mapped to a weight $w_i$ between 0 to 1 based on its dv/dt. In FIG. 8A, the number near each circle represent the weight of the slope.

Notice also in FIG. 8A, that some EP signals comprise earliest S-wave patterns, such as in signals 444 sensed by electrodes E19 and E20 (together 448). Such negative-slope patterns, without signal amplitude first rising as an EP wave approaches an electrode, are indicative of an aberrant focal EP wave propagating away from the electrodes. This condition indicates that catheter 14 is "right on target," where some of the electrodes are in vicinity of a focal source of Arrhythmia (e.g., distance 60 being smaller that a length of arm 15).

As FIG. 8B illustrates, estimated location 446 of a focal source, derived using a weighted cost-function, is at least in part surrounded by measured locations of electrodes 16.

The required alternation in the set of equations for a 2D cost-function model (i.e., Eq. 5 excluding z-dependence) is as follows:

$$J(\theta) = \frac{1}{m}\sum_{i=1}^{m} w_i \cdot (v \cdot d_i + t_0 - t_i)^2 + \frac{\lambda}{2m}\left(x_0^2 + y_0^2 + \frac{1}{v^2}\right) \quad \text{Eq. 6}$$

$$\frac{\partial J(\theta)}{\partial x_0} = -\frac{2}{m}\sum_{i=1}^{m} \frac{w_i \cdot (v \cdot d_i + t_0 - t_i)}{d_i}(x_i - x_0) + \frac{\lambda \cdot x_0}{m}$$

$$\frac{\partial J(\theta)}{\partial y_0} = -\frac{2}{m}\sum_{i=1}^{m} \frac{w_i \cdot (v \cdot d_i + t_0 - t_i)}{d_i}(y_i - y_0) + \frac{\lambda \cdot y_0}{m}$$

$$\frac{\partial J(\theta)}{\partial v} = \frac{2}{m}\sum_{i=1}^{m} w_i \cdot (v \cdot d_i + t_0 - t_i) \cdot d_i + \frac{\lambda}{m \cdot v^3}$$

$$\frac{\partial J(\theta)}{\partial t_0} = \frac{2}{m}\sum_{i=1}^{m} w_i \cdot (v \cdot d_i + t_0 - t_i)$$

In some exemplary embodiments, if estimation errors of relative times are higher than a given threshold, an iterative DOA estimation process is applied and is described in FIGS. 9A and 9B, FIGS. 10A and 10B, and FIGS. 11A and 11B.

Figure 9B:
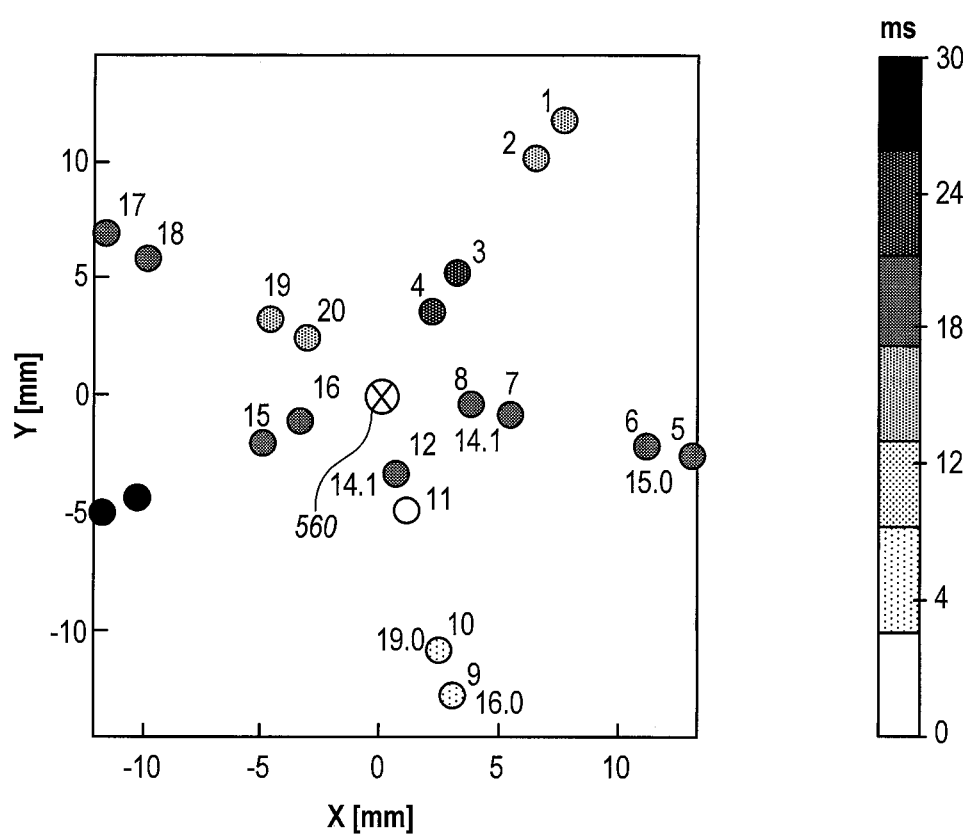

FIGS. 9A and 9B are, respectively, a plot showing graphs of unipolar EP signals having estimation errors 550 higher than a given threshold, and a respective initially estimated location 560 of the focal source in X-Y space, in accordance with an embodiment of the present invention. Furthermore, some EP values are found within a double potential LAT (such as corrected annotation value 333 of the EP signal of electrode 15 in FIG. 9A). Also, some EP values (both measured an estimated values) are found between start and end points of unipolar negative deflection (such as within negative deflection 555 of the EP signal of electrode 16 in FIG. 9A)

As seen in FIG. 9B, location 560 is very close to the location of the distal tip of the catheter, however given the above observations this location is probably wrong.

In an exemplary embodiment, if the average estimation error is above a given threshold (e.g., 7 mSec) processor 22 runs an iterative calculation to estimate the DOA. The average estimation error in FIG. 9A is 12.4 mSec. In each iteration, a local activation time with highest estimation error is removed from DOA estimation. The process is repeated as long as there are more than ten valid local activation time values.

Figure 10:
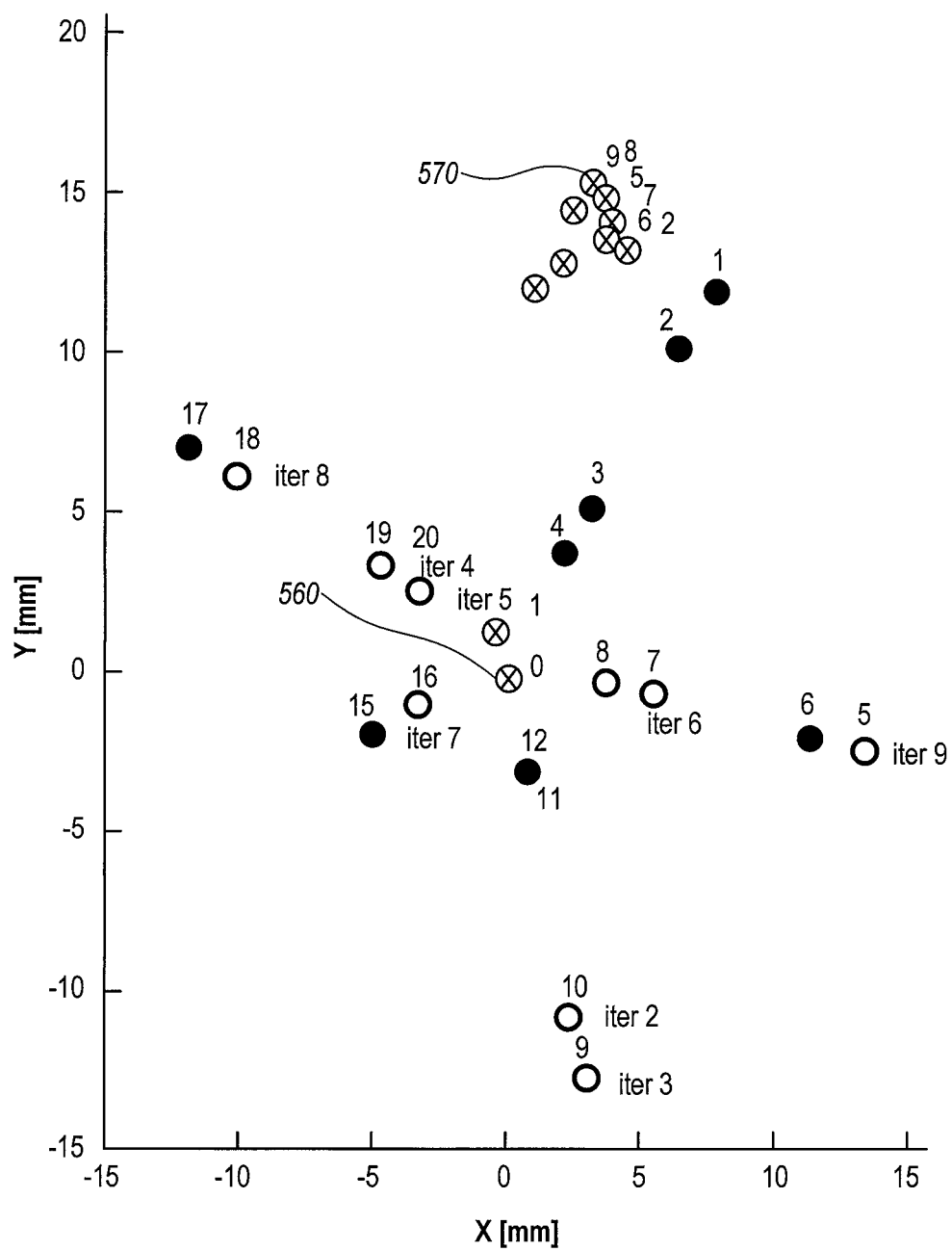
FIG. 10 is a graph showing the estimated location of focal source of FIG. 9B in nine iterations of the iterative DOA model, in accordance with an exemplary embodiment of the present invention.

FIG. 10 is a graph showing the estimated location of focal source 560 of FIG. 9B in nine iterations of the iterative DOA model, in accordance with an exemplary embodiment of the present invention. In the zero and the first iterations, focal source location 560 almost coincides with the location of distal tip 18 of the catheter, however from the second iteration to the 9th iteration the location of focal activity is shifted and finally placed (570) near electrode "1". In FIG. 10, the full circles represent valid electrodes for DOA estimation, while the ring circles represent invalid electrodes. The tagging "iter x" beside a ring electrode informs that the specific electrode was eliminated from DOA estimation at iteration x. The percentage of invalid segments is a good measure for the "complexity" of the AF in this subject.

Between the zero iteration and the 9th iteration the maximal estimation error falls from approximately 25 mSec to less than 5 mSec. The conduction velocity, CV, which also serves as an estimate of the cost in Eq. 4, drops from more than 100 mm/mSec to a minimal value of 0.5 mm/msec.

The disclosed iterative model is used in handling acquisitions having noisy waveforms or cases with more than one wave propagating toward the catheter.

First and Second Methods of Statistical Tests

A duration of a typical acquisition is 100-200 msec. A typical recording has 30 seconds of unipolar signals and thus contains approximately 120-200 acquisitions. All valid DOA estimates from the approximately 120-200 acquisitions are stored, to be subsequently aggregated, until all acquisitions are processed, and then a statistical method is applied to the corpus of valid DOA estimations.

First Statistical Method

As noted above and described in this section, processor 22 puts the aggregated DOA and distance values in histograms and statistically analyzes the histograms. In an exemplary embodiment, the processor is configured to derive from the histograms an estimated location by fitting a curve to the histograms and finding the maximum of the curve as a function of estimated DOA and distance.

Figure 11A:
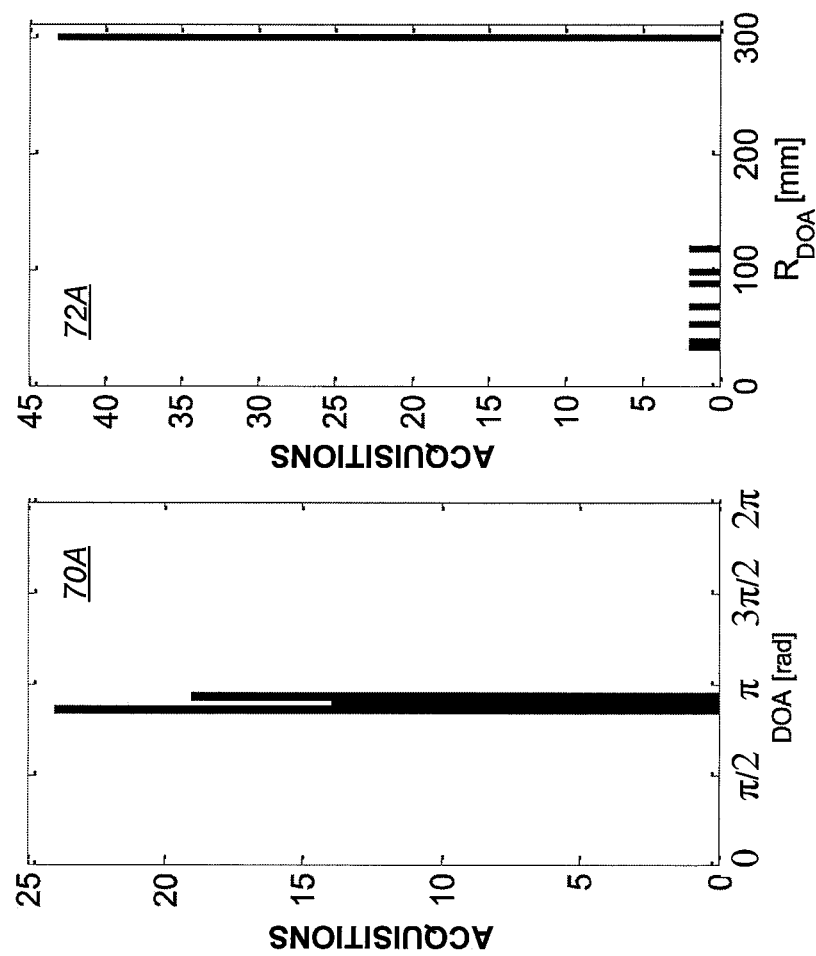
FIGS. 11A and 11B are histograms of direction of arrival (DOA) and distance from a focal source, in accordance with an exemplary embodiment of the present invention.
Figure 11B:
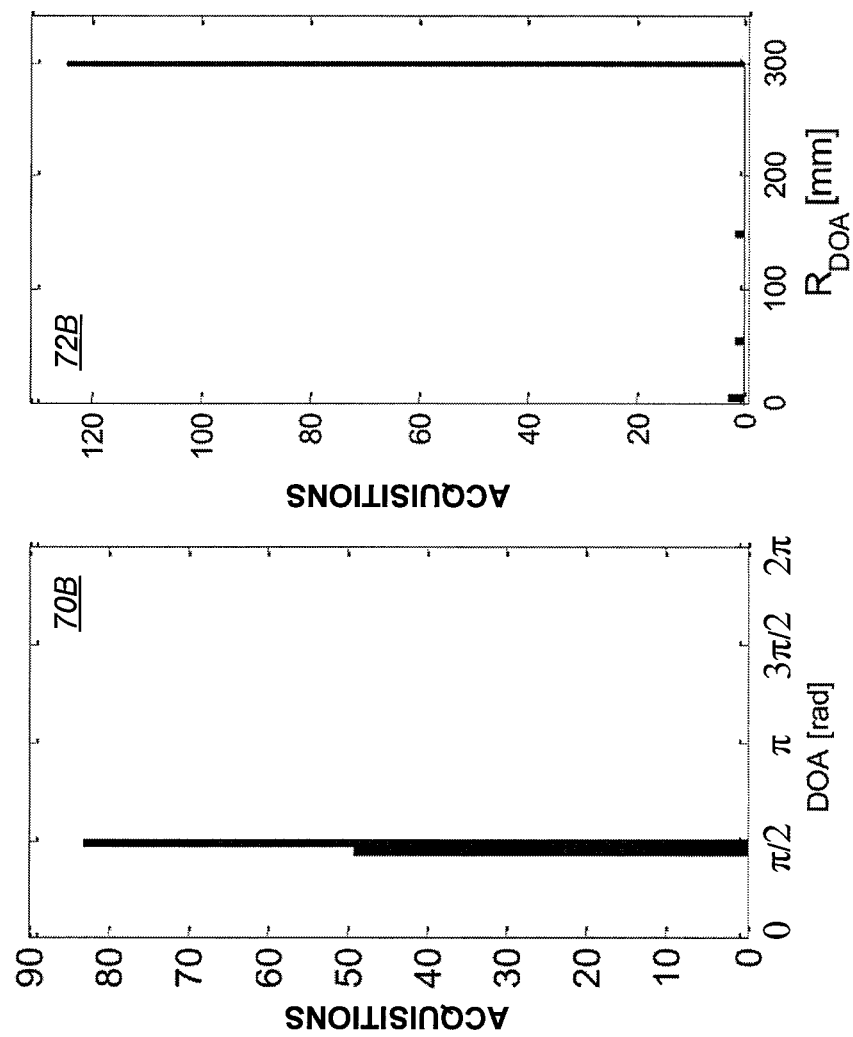

FIGS. 11A and 11B are histograms 70A and 70B of direction of arrival (DOA) and of histograms 72A and 72B of distance from a focal source, respectively, in accordance with an embodiment of the present invention. As seen, the DOA distribution consists of a number of acquisitions per DOA value, and the distance distribution consists of a number of acquisitions per distance value. Typically, processor 22 compiles (i.e., aggregates) histograms 70A and 70B and histograms 72A and 72B from a number ranging between several tens and several hundred of acquisitions that passed the pre-filtering stage, such shown in FIG. 2 and analyzed in FIG. 3.

Using a statistical test, processor 22 checks first if the DOA distribution, as shown by example in DOA histograms of FIGS. 11A and 11B, yields a consistent DOA value. Examples of consistency test tools include, but are not limited to, constancy estimator and use of confidence interval.

If DOA is found inconsistent, for example by the distribution indicating two or more substantivity different DOA values, processor 22 ends the disclosed focal source identification processes. In an embodiment, processor 22 presents a notice to a user that the process did not identify a focal source of arrhythmogenic activity.

If processor 22 derives a consistent DOA value from the acquisition distribution as a function of DOA, then processor 22 best estimates from the distributions a DOA and s distance to a focal source in question. Processor 22 then uses the best estimated DOA and distance to identify a location of a focal source of arrhythmogenic activity in heart 12 that generated the received EP signals.

As seen in FIG. 11A, most prevalent DOA values of the clinical case analyzed by histogram 70A of FIG. 11A fall about a DOA of $0.85\pi$. The respective most common distance indicated by histogram 72A is about 300 mm. Processor 22 can therefore identify, for that patient, an exitance of a location of focal arrhythmia at a distance of about 300 mm from the location of distal tip 18, at an angle of $0.85\pi$ relative to the X-axis.

FIG. 11B shows that most prevalent DOA values of the clinical case analyzed by histogram 70B of FIG. 11B fall about a DOA of $0.5\pi$. The respective most common distance indicated by histogram 72B is about 300 mm. Processor 22 can therefore identify, for that patient, an exitance of a location of focal arrhythmia at a distance of about 300 mm from the location of distal tip 18, at an angle of $0.5\pi$ relative to the X-axis.

Second Statistical Method

Figure 12:
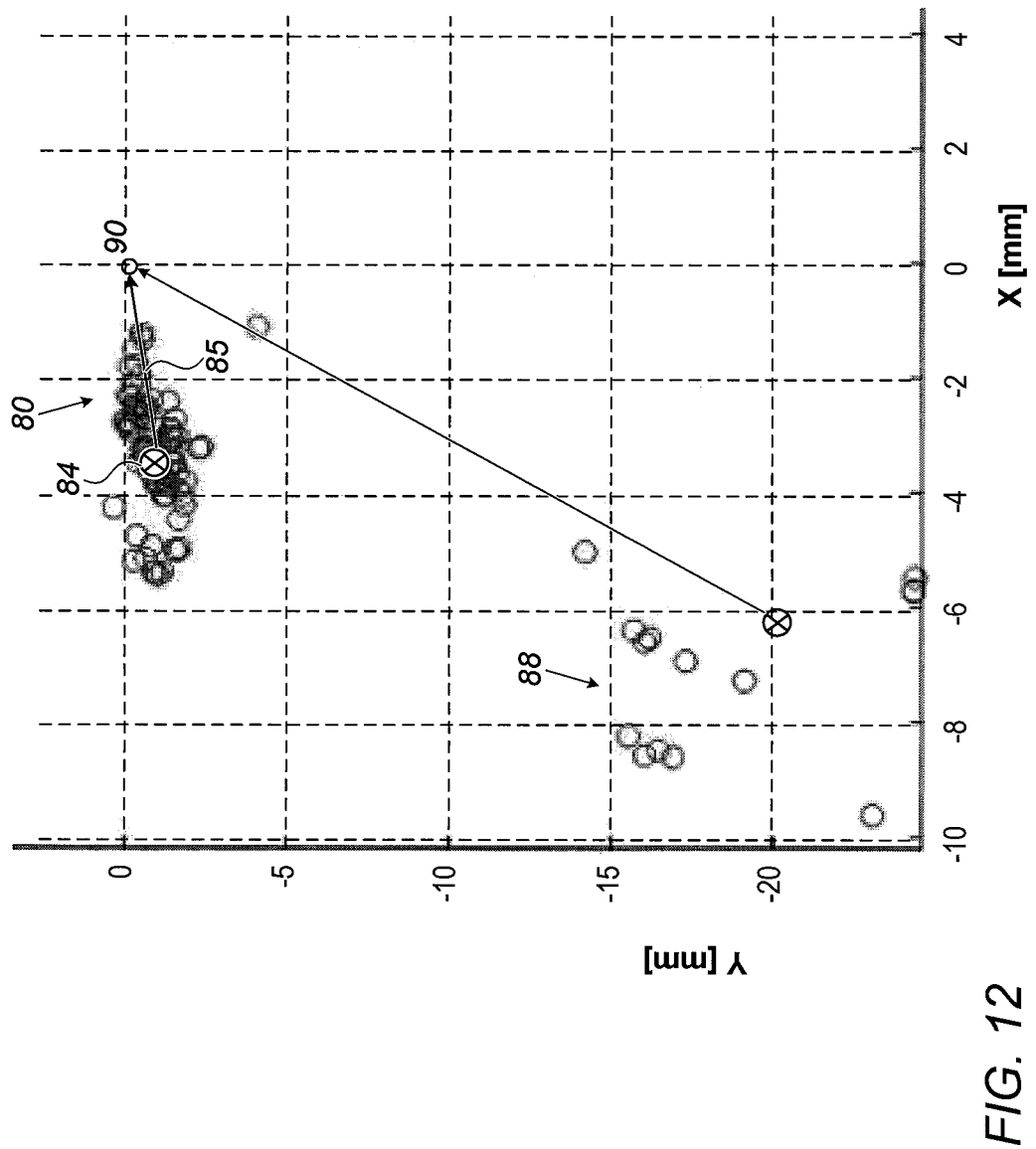
FIG. 12 is a plot showing DOA clusters analyzed by a k-means clustering model, in accordance with an exemplary embodiment of the present invention.

FIG. 12 is a plot showing DOA clusters analyzed by a k-means clustering model, in accordance with an embodiment of the present invention. The k-means clustering model was applied by processor 22 to a set of DOA values that passed pre-filtering and were aggregated in X-Y space.

In FIG. 12, circle represents DOA estimation from an acquisition of LAT values of the numerous acquisitions included in a single recording session. In the shown recording results, there are two clusters of DOA that "explains" the data. A first cluster 80 (red circle at (−3.7 mm, −0.2 mm)) contains 80.5% of the DOAs and a second cluster 88 has 19.5% of contains 19.5% of DOA in the recording.

If an estimated location of one of the dominant clusters (more than 10% of DOA segments) could be projected to the anatomy i.e. the distance from an estimated location, such as an estimated location 84, to the anatomy is less than a given value, e.g., 6 mm, (configurable) then a focal source is identified. As seen in FIG. 12, the distance from the k-means clustering estimated location 84 to an anatomy location 90, given by the length of an arrow 85 is about 3 mm, well below the 6 mm upper limit. Hence location 90 was validated by the disclosed technique as a focal source.

Focal source may also be validated if we find at least 10 indications (configurable) of earliest S-wave patterns in electrodes located within a radius of 6 mm from the focal. It's important to note that foci detection based DOA could manifested in location on the anatomy without placing a catheter in the area of the focal activity, therefore the validation process is optional.

Although the embodiments described herein mainly address cardiac applications, the methods and systems described herein can also be used in other applications, such as in neurology. The disclosed methods could also be applied with in any dataset that involves spatiotemporal "cues" for focal activity and a processor is required find this focal activity, for example, for focal estimation of epileptic patients using EEG/MEG.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for automatically identifying a location of focal arrhythmogenic activity, the method comprising:
   receiving, via a plurality of electrodes in a heart, a collection of acquisitions, wherein each acquisition comprises a set of electrophysiological (EP) signals measured by the electrodes;
   estimating for each of the acquisitions a respective direction of arrival (DOA) and a respective distance relative to the electrodes, from which the set of EP signals originated;
   aggregating the acquisitions, to form a statistical distribution of the acquisitions as a function of estimated DOA and distance;
   checking, using a statistical test, whether the statistical distribution of the acquisitions is consistent, in accordance with a predefined consistency criterion;
   deriving from the statistical distribution an estimated location in the heart of a focal source of an arrhythmogenic activity that generated the received EP signals when the statistical distribution of the acquisitions is found consistent;
   overlaying the estimated location of the focal source on an anatomical map of at least a portion of the heart; and
   presenting to a user a notification that a location of focal arrhythmogenic activity was not identified when the statistical distribution of the acquisitions is found to be inconsistent.

2. The method according to claim 1, wherein, for a given acquisition, estimating the DOA and distance comprises extracting from the set of EP signals in the given acquisition a respective set of relative times of arrival, and estimating the DOA and distance using the extracted relative times of arrival.

3. The method according to claim 2, wherein aggregating the acquisitions comprises pre-filtering the acquisitions according to the respective set of relative times of arrival extracted from each acquisition, and including in the statistical distribution of the acquisitions only the pre-filtered acquisitions.

4. The method according to claim 3, wherein pre-filtering the acquisitions according to the extracted set of relative times of arrival comprises the steps of:
   using the estimated DOA and distance, calculating for each acquisition a modeled set of relative times of arrival that would have resulted from an EP wave originating from a focal source at the estimated DOA and distance; and
   for each acquisition, determining, by applying a predefined geometrical test, a degree of similarity between the extracted set and modeled set of relative times of arrival.

5. The method according to claim 4, wherein estimating the degree of similarity comprises calculating a cosine-similarity geometrical test between the two sets.

6. The method according to claim 4, wherein estimating the degree of similarity comprises calculating an estimation error for each relative time of arrival and comparing the estimation error to a given threshold.

7. The method according to claim 4, and comprising, using the modeled set of relative times of arrival, adjusting time values of annotations over EP signals for which a voltage-time slope of the EP signal is shallower than a prespecified slope.

8. The method according to claim 4, wherein pre-filtering the acquisitions comprises discarding one or more acquisitions determined to have dissimilar sets of times of arrival.

9. The method according to claim 1, wherein deriving the estimated location comprises fitting a curve to the statistical distribution and finding a maximum of the curve as a function of estimated DOA and distance.

10. The method according to claim 1, wherein estimating the DOA and the distance comprises minimizing a cost-function.

11. The method according to claim 10, wherein minimizing the cost-function comprises minimizing a weighted cost-function.

12. The method according to claim 10, wherein minimizing the cost-function comprises minimizing the cost-function iteratively, by removing in each iteration an EP signal value having a largest estimation error.

13. The method according to claim 1, wherein deriving the estimated location comprises applying k-means analysis to the statistical distribution, projecting estimated locations on anatomy and selecting the location having a projected distance that is less than a given value.

14. A system for automatically identifying a location of focal arrhythmogenic activity, the system comprising:
an interface, configured to receive a collection of acquisitions acquired by a plurality of electrodes in a heart, wherein each acquisition comprises a set of electrophysiological (EP) signals; and
a processor, which is configured to:
estimate for each of the acquisitions a respective direction of arrival (DOA) and a respective distance relative to the electrodes, from which the set of EP signals originated;
aggregate the acquisitions, to form a statistical distribution of the acquisitions as a function of estimated DOA and distance;
check, using a statistical test, whether the statistical distribution of the acquisitions is consistent, in accordance with a predefined consistency criterion;
derive from the statistical distribution an estimated location in the heart of a focal source of an arrhythmogenic activity that generated the received EP signals when the statistical distribution of the acquisitions is found consistent;
overlay the estimated location of the focal source on an anatomical map of at least a portion of the heart; and
present to a user a notification that a location of focal arrhythmogenic activity was not identified when the statistical distribution of the acquisitions is found to be inconsistent.

15. The system according to claim 14, wherein, for a given acquisition, the processor is configured to estimate the DOA and distance by extracting from the set of EP signals in the given acquisition a respective set of relative times of arrival, and estimating the DOA and distance using the extracted relative times of arrival.

16. The system according to claim 15, wherein, in aggregating the acquisitions, the processor is configured to pre-filter the acquisitions according to the respective set of relative times of arrival extracted from each acquisition, and to include in the statistical distribution of the acquisitions only the pre-filtered acquisitions.

17. The system according to claim 16, wherein the processor is configured to pre-filter the acquisitions according to the extracted set of relative times of arrival by performing the steps of:
using the estimated DOA and distance, calculating for each acquisition a modeled set of relative times of arrival that would have resulted from an EP wave originating from a focal source at the estimated DOA and distance; and
for each acquisition, determining, by applying a predefined geometrical test, to what degree the extracted set and modeled set of relative times of arrival are similar.

18. The system according to claim 17, wherein the processor is configured to estimate to what degree the extracted set and modeled set of relative times of arrival are similar by calculating a cosine-similarity geometrical test between the two sets.

19. The system according to claim 17, wherein the processor is configured to estimate a degree of similarity between the extracted set and modeled set of relative times of arrival, by calculating an estimation error for each relative time of arrival and comparing the estimation error to a given threshold.

20. The system according to claim 17, wherein the processor is further configured to, using the modeled set of relative times of arrival, adjust time values of annotations over EP signals for which a voltage-time slope of the EP signal is shallower than a prespecified slope.

21. The system according to claim 20, wherein, in pre-filtering the acquisitions, the processor is configured to discard one or more acquisitions determined to have dissimilar sets of times of arrival.

22. The system according to claim 14, wherein the processor is configured to derive the estimated location by fitting a curve to the statistical distribution and finding a maximum of the curve as a function of estimated DOA and distance.

23. The system according to claim 14, wherein the processor is configured to estimate the DOA and the distance by minimizing a cost-function.

24. The system according to claim 23, wherein the processor is configured to minimize the cost-function by minimizing a weighted cost-function.

25. The system according to claim 23, wherein the processor is configured to minimize the cost-function iteratively, by removing in each iteration an EP signal value having largest estimation error.

26. The system according to claim 14, wherein the processor is configured to derive the estimated location by applying k-means analysis to the statistical distribution, projecting estimated locations on anatomy and selecting the location having a projected distance that is less than a given value.

* * * * *